US012686727B2

(12) United States Patent
Whisstock et al.

(10) Patent No.: US 12,686,727 B2
(45) Date of Patent: Jul. 21, 2026

(54) ANTIBODIES FOR BINDING PLASMIN

(71) Applicant: MONASH UNIVERSITY, Clayton (AU)

(72) Inventors: James Whisstock, Clayton (AU); Ruby Law, Clayton (AU); Adam Quek, Clayton (AU); Paul Conroy, Clayton (AU); Guojie Wu, Clayton (AU)

(73) Assignee: Monash University, Clayton (AU)

( * ) Notice: Subject to any disclaimer, the term of this patent is extended or adjusted under 35 U.S.C. 154(b) by 1005 days.

(21) Appl. No.: 17/772,090

(22) PCT Filed: Oct. 28, 2020

(86) PCT No.: PCT/AU2020/051164
§ 371 (c)(1),
(2) Date: Apr. 26, 2022

(87) PCT Pub. No.: WO2021/081582
PCT Pub. Date: May 6, 2021

(65) Prior Publication Data
US 2023/0220112 A1      Jul. 13, 2023

(30) Foreign Application Priority Data

Oct. 28, 2019      (AU) ................................ 2019904049

(51) Int. Cl.
*C07K 16/40*      (2006.01)
*A61P 7/00*       (2006.01)

(52) U.S. Cl.
CPC ................ *C07K 16/40* (2013.01); *A61P 7/00* (2018.01); *C07K 2317/565* (2013.01); *C07K 2317/567* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 5,888,749 | A | 3/1999 | Soe et al. |
| 2003/0180934 | A1 | 9/2003 | Ni et al. |
| 2019/0085097 | A1 | 3/2019 | Reed |

FOREIGN PATENT DOCUMENTS

| | | |
|---|---|---|
| EP | 0251186 | 9/1993 |
| EP | 3459974 | 3/2019 |
| JP | S633795 A | 1/1998 |
| WO | WO 1989/012098 | 12/1989 |
| WO | WO 2005/116077 A2 | 12/2005 |
| WO | WO 2006/050177 A2 | 5/2006 |
| WO | WO 2015/007727 A1 | 1/2015 |
| WO | WO 2020/099508 A1 | 5/2020 |

OTHER PUBLICATIONS

Yang et al. The Journal of Immunology, vol. 172, Issue 9, May 2004, pp. 5765-5773.*
Schroeder et al. (J Allergy Clin Immunol 2010, 125:S41-S52).*
Lloyd et al. (Protein Engineering, Design & Selection 2009, 22:159-168).*
Rudikoff et al. (Proc Natl Acad Sci USA 1982 vol. 79 p. 1979).*
Pascalis et al. (The Journal of Immunology (2002) 169, 3076-3084).*
Casset et al. (BBRC 2003, 307:198-205).*
Vajdos et al. (J. Mol. Biol. (2002) 320, 415-428).*
Chen et al. (J. Mol. Bio. (1999) 293, 865-881).*
Wu et al. (J. Mol. Biol. (1999) 294, 151-162).*
Padlan et al. (PNAS 1989, 86:5938-5942).*
Lamminmaki et al. (JBC 2001, 276:36687-36694).*
Piche-Nicholas et al. MABS 2018, 10:81-94.*
Wang et al., "Crystal structure of the catalytic domain of human plasmin complexed with streptokinase," Science, Sep. 1998, 281(5383):1662-5.
Andreoni et al., "Immunoglobulin Attenuates Streptokinase-Mediated Virulence in *Streptococcus dysgalactiae* Subspecies equisimilis Necrotizing Fasciitis", J Infect Dis., (2018), 217(2):270-279.
Burkovitz et al., "Understanding differences between synthetic and natural antibodies can help improve antibody engineering," Mabs, Feb. 17, 2016, 8(2):278-87.
Jasion et al., "Survival and digestibility of orally-administered immunoglobulin preparations containing IgG through the gastrointestinal tract in humans," Nutrition Journal, Dec. 2015, 14(1):1-8.
Kelly et al., "Survival of anti-Clostridium difficile bovine immunoglobulin concentrate in the human gastrointestinal tract," Antimicrobial Agents and Chemotherapy, Feb. 1997, 41(2):236-41.
Lijnen et al., "Screening panels of monoclonal antibodies using phage-displayed antigen," Analytical Biochemistry, Jun. 1, 1997, 248(2):211-5.
McArthur et al., "The role of streptokinase as a virulence determinant of *Streptococcus pyogenes*—potential for therapeutic targeting," Current Drug Targets, Mar. 1, 2012, 13(3):297-307.
Nishiya et al., "Determination of a factor VIII-interactive region within plasmin responsible for plasmin-catalysed activation and inactivation of factor VIII (a)," Thrombosis and Haemostasis, Apr. 2010, 104(07):105-17.
Nitzsche et al., "*Streptococcus pyogenes* triggers activation of the human contact system by streptokinase," Infection and Immunity, Aug. 2015, 83(8):3035-42.
Okumura et al., "The extracellular processing of HIV-1 envelope glycoprotein gp160 by human plasmin," FEBS Letters, Jan. 1999, 442(1):39-42.
PCT International Search Report and Written Opinion in International Appln. No. PCT/AU2020/051164, dated Dec. 24, 2020, 7 pages.

(Continued)

*Primary Examiner* — Sharon X Wen
(74) *Attorney, Agent, or Firm* — Fish & Richardson P.C.

(57) ABSTRACT

The present invention provides an antigen binding protein comprising an antigen binding domain that binds to plasmin, wherein the antigen binding protein reduces the activity of plasmin. The invention also provides compositions comprising the antigen binding protein, and uses and method of treatment comprising the same.

13 Claims, 10 Drawing Sheets
Specification includes a Sequence Listing.

(56)　　　　　　References Cited

OTHER PUBLICATIONS

Rox et al., "Linoleic and palmitoleic acid block streptokinase-mediated plasminogen activation and reduce severity of invasive group A streptococcal infection," Scientific Reports, Sep. 18, 2017, 7(1):1-2.

Siemens et al., "*Streptococcus pyogenes* M49 Plasminogen/Plasmin Binding Facilitates Keratinocyte Invasion via Integrin-Integrin-linked Kinase (ILK) Pathways and Protects from Macrophage Killing," Journal of Biological Chemistry, Jun. 17, 2011, 286(24):21612-22.

Smiley et al., "Yersinia pestis Pla Protein Thwarts T Cell Defense against Plague," Infection and Immunity, May 1, 2019, 87(5):e00126-19.

Su et al., "Effect of annexin II-mediated conversion of plasmin from plasminogen on airborne transmission of HON2 avian influenza virus," Veterinary Microbiology, Sep. 1, 2018, 223:100-6.

Sugimura et al., "Plasmin modulators, aprotinin and anti-catalytic plasmin antibody, efficiently inhibit destruction of bovine vascular endothelial cells by choriocarcinoma cells," Gynecologic Oncology, Mar. 1, 1994, 52(3):337-46.

Sumitomo et al., "Group A *Streptococcus* exploits human plasminogen for bacterial translocation across epithelial barrier via tricellular tight junctions," Scientific Reports, Jan. 29, 2016, 6(1):1-4.

Xue et al., "Crystal Structure of the native plasminogen reveals an activation-resistant compact conformation," Journal of Thrombosis and Haemostasis, Jul. 2012, 10(7):1385-96.

Zhao et al., "Termination of bleeding by a specific, anticatalytic antibody against plasmin," Journal of Thrombosis and Haemostasis, Sep. 2019, 17(9):1461-9.

* cited by examiner

FIGs. 1A-C
A
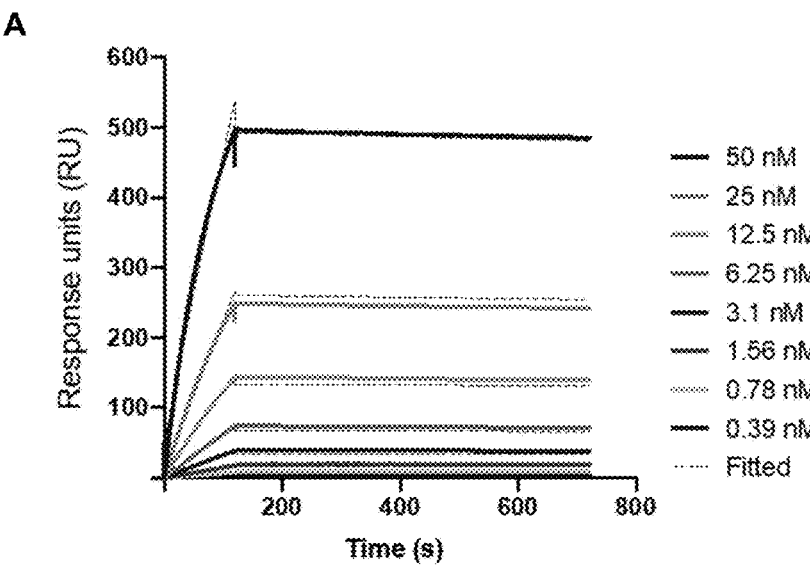
B
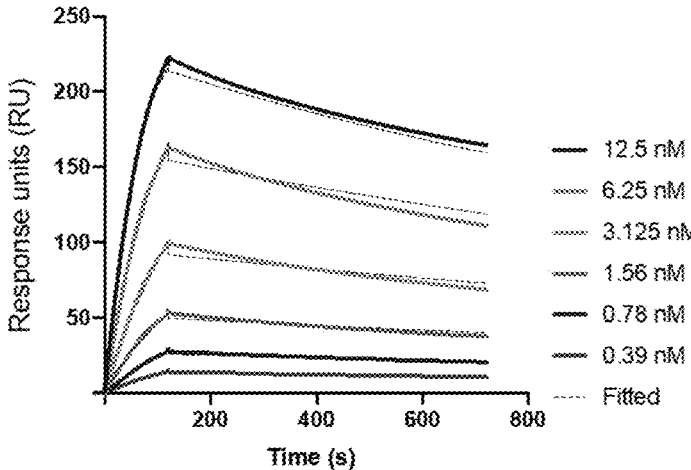
C
| B10 | $K_a$ (M$^{-1}$.s$^{-1}$) | $K_d$ (s$^{-1}$) | $K_D$ (nM) |
|---|---|---|---|
| Plasminogen | $4.16 \pm 2.0\ e^{+5}$ | $4.9 \pm 0.16\ e^{-5}$ | $0.5 \pm 0.2$ |
| Plasmin | $8.4 \pm 0.38\ e^{+5}$ | $4.3 \pm 0.2\ e^{-4}$ | $0.5 \pm 0.1$ |

FIG. 2
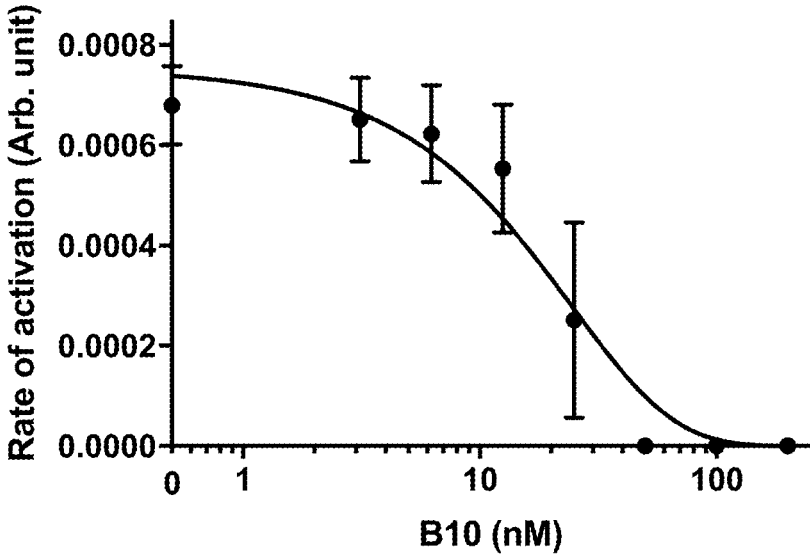
$$IC_{50} = 21.51 \pm 2.28 \text{ nM}$$
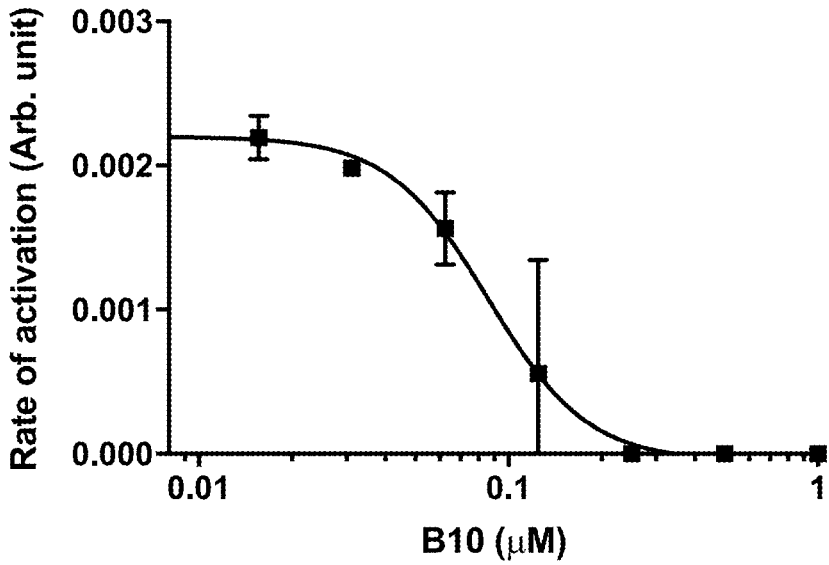
$$IC_{50} = 86.0 \pm 11.6 \text{ nM}$$

FIGs. 4A-B
A
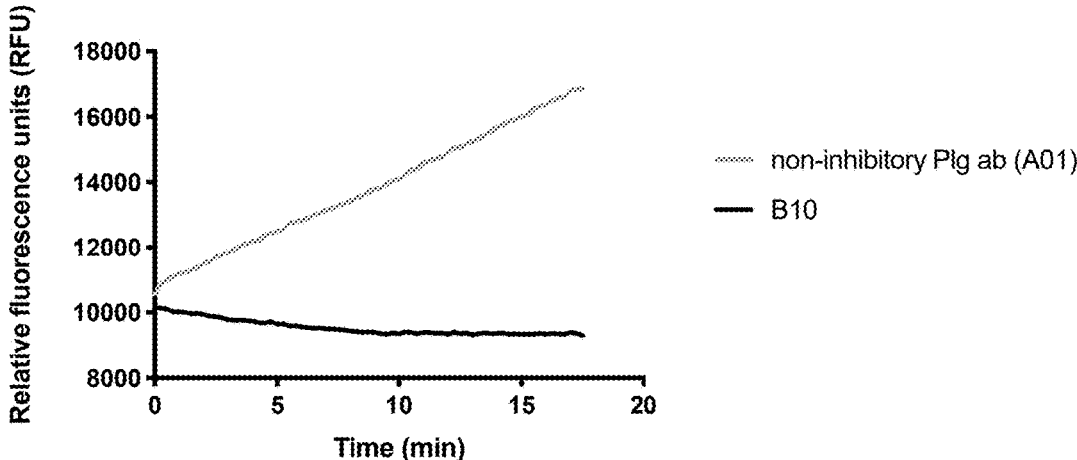
B
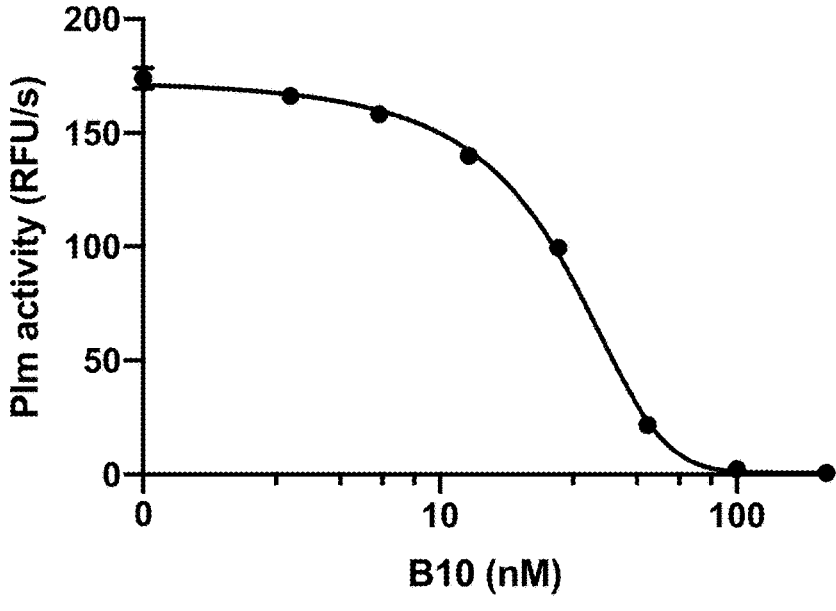

FIGs. 5A-B
A
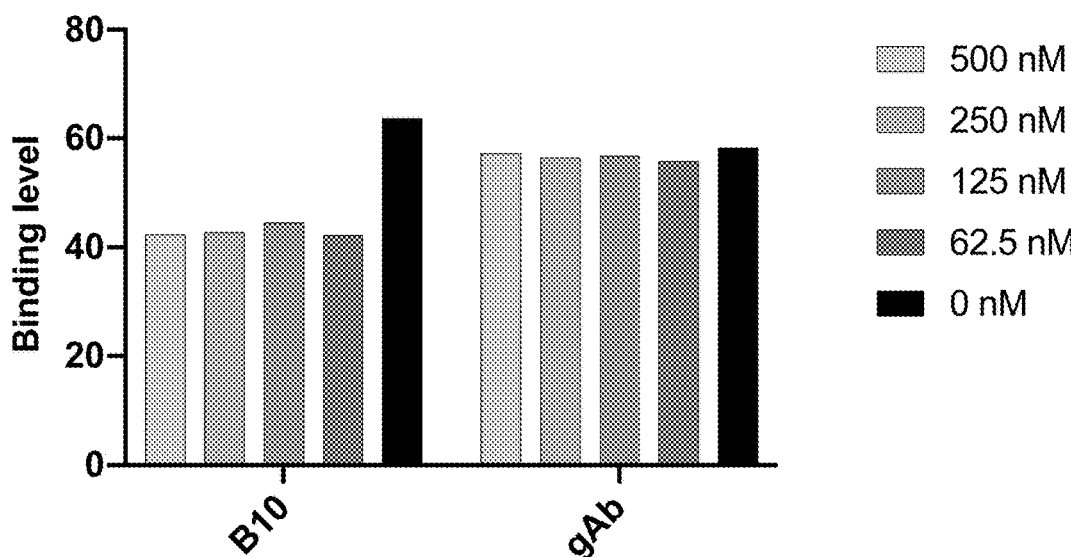
B
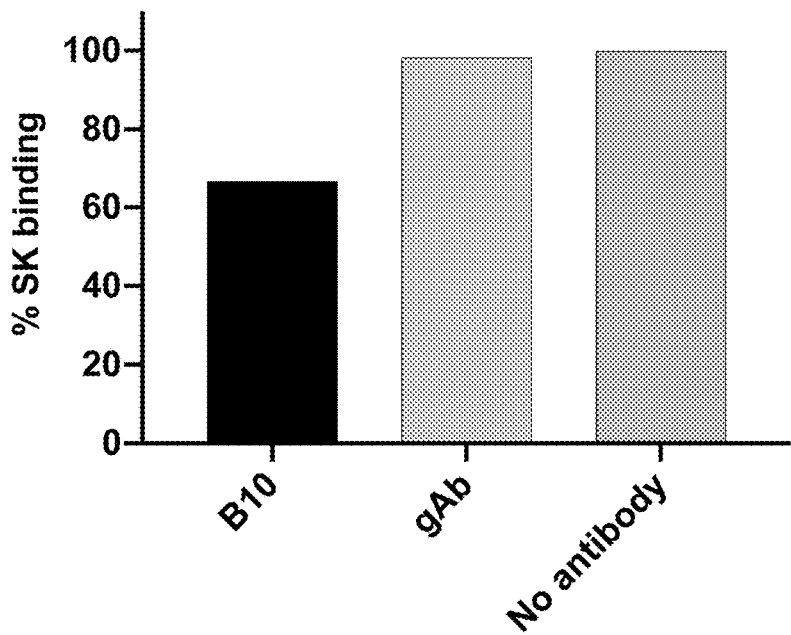

FIG. 7
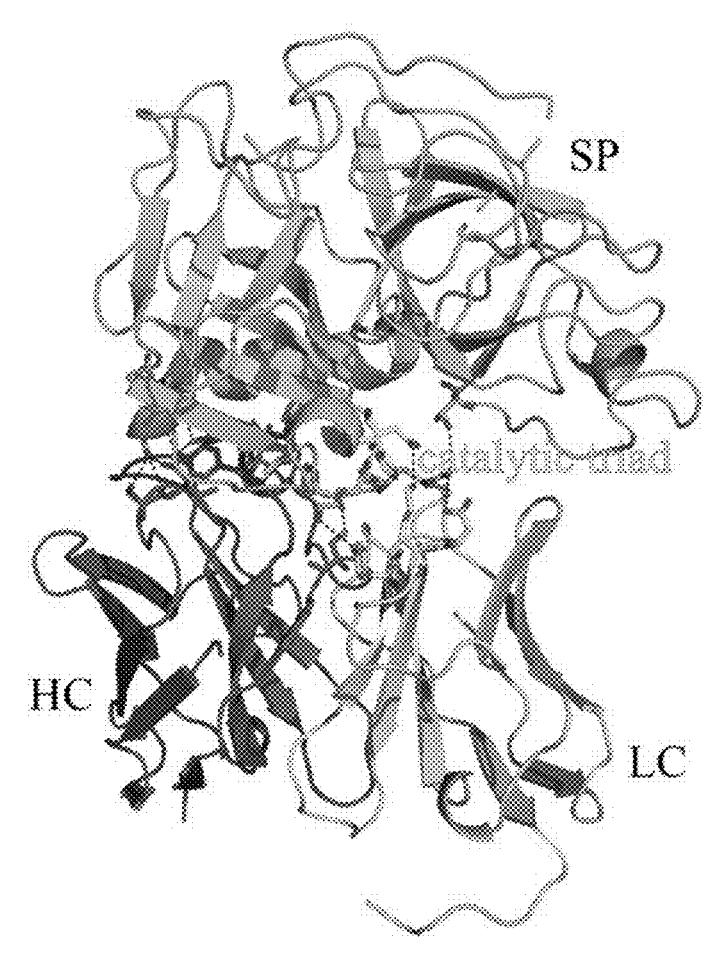
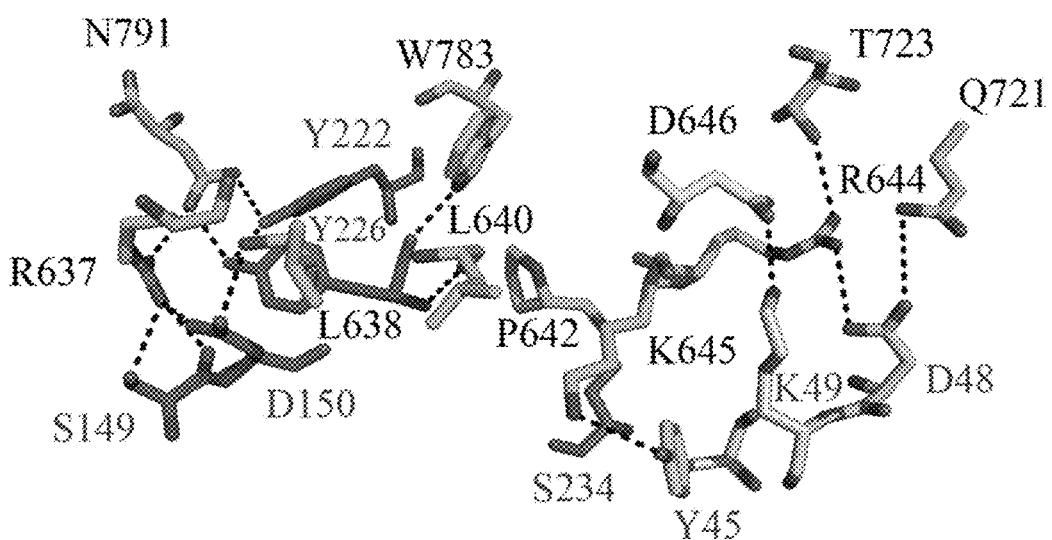

FIG. 8
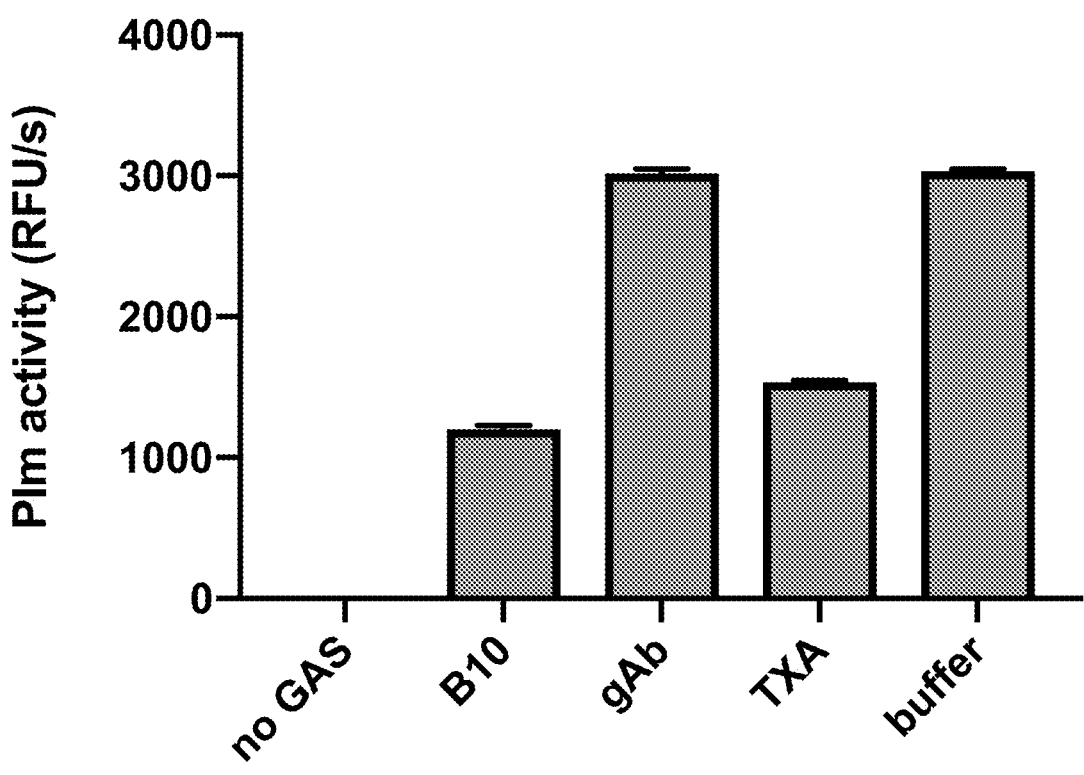
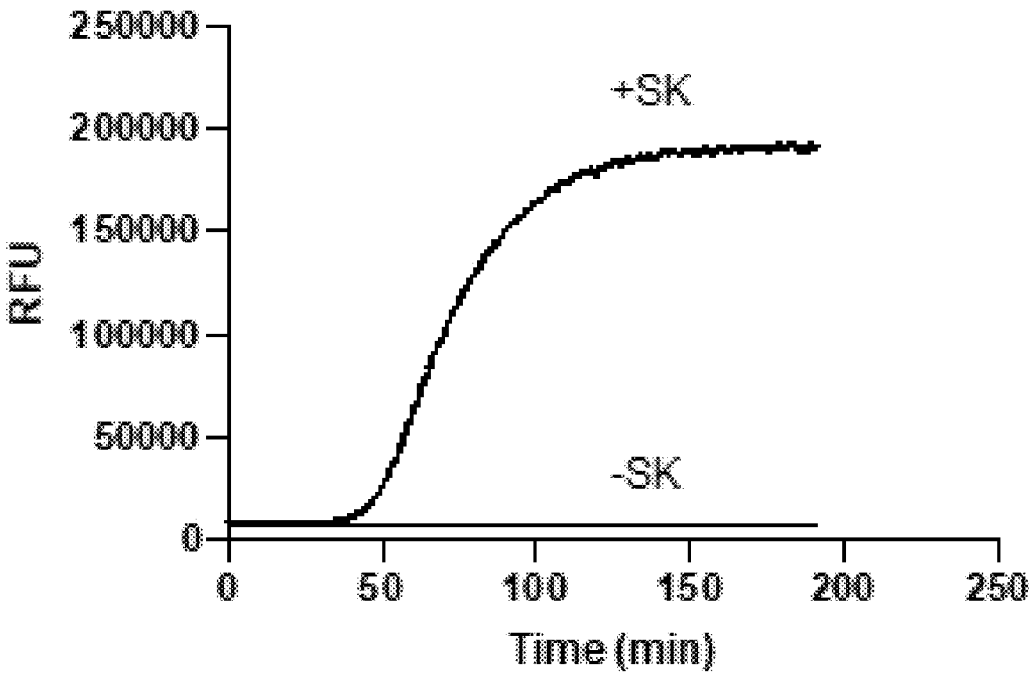

ANTIBODIES FOR BINDING PLASMIN

FIELD OF THE INVENTION

The invention relates to antigen binding proteins and related fragments thereof for binding to plasmin, to production of said antigen binding proteins and fragments and to use of said antibodies and fragments for detection and therapy of various conditions.

RELATED APPLICATIONS

This application is a U.S. National Stage Application under 35 U.S.C. § 371 of International Application Serial No. PCT/AU2020/051164, filed on Oct. 28, 2020, which claims priority from Australian provisional application no. AU 2019904049, filed on Oct. 28, 2019, the contents of which are incorporated herein by reference in their entirety.

SEQUENCE LISTING

This application contains a Sequence Listing that has been submitted electronically as an ASCII text file named "Sequence_Listing.txt." The ASCII text file, created on Apr. 26, 2022, is 20 kilobytes in size. The material in the ASCII text file is hereby incorporated by reference in its entirety.

BACKGROUND OF THE INVENTION

Plasminogen (PLG) is the inactive zymogen form of plasmin, a serine protease that has a broad specificity for target substrates that include fibrin, fibrinogen, complement components 3 and 5 (C3 and C5), vitronectin, osteocalcin, factors V, VIII and X and some collagenases. Thus, PLG and PLM together are involved in various important physiological and pathological processes including fibrinolysis and haemostasis, degradation of extracellular matrix, cell migration, embryonic development, tissue remodelling, inflammation, wound healing, angiogenesis and tumour invasion.

PLG is synthesized primarily in the liver, but also in major organs and tissues. Consequently, PLG is found in significant quantities in plasma and many extravascular fluids. Under physiological conditions, PLG is converted to the active form, plasmin (PLM), through cleavage in the activation loop. Activation can be mediated by urokinase plasminogen activator (uPA) or tissue plasminogen activator (tPA), or by various other proteases, and converts the single-chain PLG (amino acid residues 20-810) to PLM which consists of disulfide bond-linked heavy chain A (residues 20-580) and light chain B (residues 581-810). Heavy chain A contains 5 kringle domains (which mediate binding to substrates via lysine-binding regions) and light chain B corresponds to the serine protease domain. A fragment consisting of the first 4 kringle domains has been named as angiostatin, a novel angiogenesis inhibitor.

The plasminogen/plasmin system has been implicated in a variety of physiological and pathological processes such as fibrinolysis, tissue remodelling, cell migration, inflammation, and tumour invasion and metastasis. Hereditary defects of plasminogen are a predisposing risk factor for thromboembolic disease.

There is a need for compositions and methods for modulating the plasmin system for the treatment and/or prevention of various conditions.

Reference to any prior art in the specification is not an acknowledgment or suggestion that this prior art forms part of the common general knowledge in any jurisdiction or that this prior art could reasonably be expected to be understood, regarded as relevant, and/or combined with other pieces of prior art by a skilled person in the art.

SUMMARY OF THE INVENTION

The present invention provides an antigen binding protein comprising an antigen binding domain that binds to plasmin, wherein the antigen binding protein reduces the activity of plasmin.

Preferably, the plasmin is human plasmin.

In any aspect of the present invention, an antigen binding protein of the invention binds to the serine protease domain of plasmin.

Preferably, the antigen binding protein of the invention binds to the catalytic site of the plasmin serine protease domain. The catalytic site comprises $His_{603}$, $Asp_{646}$ and $Ala/Ser_{741}$ (numbering as per human plasmin, as set forth in SEQ ID NO: 33). Preferably, the antigen binding protein binds to a peptide comprising the sequence set forth in SEQ ID NO: 34, or a fragment thereof.

In any aspect of the present invention, an antigen binding protein of the invention binds to one or more residues of a serine protease domain of plasmin at a position, or position equivalent to, $Arg_{637}$, $Leu_{638}$, $Leu_{640}$, $Pro_{642}$, $Arg_{644}$, $Lys_{645}$, $Gln_{721}$, $Trp_{783}$, and $Asn_{791}$. Preferably, the antigen binding protein of the invention binds to one or more residues of a serine protease domain of plasmin at a position, or position equivalent to, those shown in Table 2. More preferably, the residues of the antigen binding protein that bind to the one or more residues of a serine protease domain of plasmin are one or more of the amino acid residues as defined in Table 2.

The present invention also provides an antigen binding protein (e.g., antibody) that has the same amino acids at the positions, or equivalent positions to the residues specified for the B10 antibody in Table 2.

In any aspect of the present invention, an antigen binding protein of the invention may also bind to plasminogen. However, it will be understood that since plasminogen is an inactive form of the zymogen, the antigen binding protein of the invention does not inhibit activation of plasminogen, but instead inhibits activity of plasminogen that has been activated to plasmin.

In certain aspects of the invention, the antigen binding protein of the invention inhibits binding of the plasminogen activator, streptokinase, to plasminogen, and activation of plasminogen by streptokinase.

In any aspect of the present invention, the interaction of a residue of an antigen binding protein of the invention with a residue of plasmin may be defined by x-ray crystallography and a contact distance analysis of 0 to 3.9 Å (inclusive).

The present invention also provides an antigen binding protein that binds to the same epitope on plasmin as an antibody that comprises a VH domain comprising the amino acid sequence as set forth in SEQ ID NO: 8 and a VL domain comprising the amino acid sequence as set forth in SEQ ID NO: 7, wherein the antigen binding protein reduces or inhibits the activity of plasmin. In one embodiment, the epitope is defined by x-ray crystallography. Preferably, the epitope is defined by x-ray crystallography and a contact distance analysis of 0 to 3.9 Å (inclusive). Preferably, the antigen binding protein covers a surface area of plasmin of SEQ ID NO: 33 of 925 Å²±5%.

In any aspect of the present invention, an antigen binding protein of the invention may bind to plasmin and exhibit a $k_a$ ($M^{-1}s^{-1}$) of greater than about $1\times10^4$, greater than about $5\times10^4$, greater than about $1\times10^5$ or greater than or equal to about $5\times10^5$ or any value as described herein. Preferably, the antigen binding protein of the invention binds to plasmin and exhibits a $k_a$ $(M^{-1}s^{-1})$ of about $8\times10^5$.

In any aspect of the present invention, an antigen binding protein of the invention may bind to plasmin and exhibit a $k_d(s^{-1})$ of less than about $1\times10^{-3}$, or less than about $5\times10^{-4}$. Preferably, the antigen binding protein of the invention binds to plasmin and exhibits a $k_d$ $(s^{-1})$ of about $4.5\times10^{-4}\pm0.2$ or any value as described herein.

In any aspect of the present invention, an antigen binding protein of the invention may bind to plasmin and exhibit a $K_D$ of less than 2 mM, less than 100 μM, less than about 100 nM, or less than or equal to about 500 μM. Preferably, the $K_D$ is determined using any assay as described herein, for example surface plasmon resonance (SPR) including multi-cycle SPR.

An antigen binding protein of the invention may bind to a peptide derived from SEQ ID NO: 33. For example, the antigen binding protein of the invention may bind to a peptide consisting of 4, 5, 7, 8, 9, 10 or more contiguous amino acid residues of the sequence of SEQ ID NO: 33. More preferably, the antigen binding protein of the invention may bind to a peptide consisting of 4, 5, 7, 8, 9, 10 or more contiguous amino acid residues of the sequence of SEQ ID NO: 34. In some embodiments, the antigen binding protein of the invention binds to a peptide comprising, consisting essentially of or consisting of residues of 637 to 791 of SEQ ID NO: 33. More preferably, the antigen binding protein binds to at least residues $His_{603}$, $Asp_{646}$ and $Ala/Ser_{741}$ according to the sequence of plasmin set forth in SEQ ID NO: 33.

In any aspect of the present invention, the antigen binding protein does not significantly reduce or inhibit the activity of any one or more of tPA, thrombin, trypsin, Factor Xa (FXa) and plasma kallikrein.

In any embodiment, the antigen binding protein of the invention does not specifically bind to the serine-proteases trypsin, thrombin, activated protein C, kallikrein, neutrophil elastase, or combinations thereof.

The invention provides an antigen binding protein for binding to plasmin, the antigen binding protein comprising:
FR1-CDR1-FR2-CDR2-FR3-CDR3-FR4, and
FR1a-CDR1a-FR2a-CDR2a-FR3a-CDR3a-FR4a
wherein:
FR1, FR2, FR3 and FR4 are each framework regions;
CDR1, CDR2 and CDR3 are each complementarity determining regions;
FR1a, FR2a, FR3a and FR4a are each framework regions;
CDR1a, CDR2a and CDR3a are each complementarity determining regions;
wherein the sequence of any of the framework regions or complementarity determining regions are as described herein.

The invention provides an antigen binding protein for binding to plasmin, the antigen binding protein including:
FR1-CDR1-FR2-CDR2-FR3-CDR3-FR4, and
FR1a-CDR1a-FR2a-CDR2a-FR3a-CDR3a-FR4a
wherein:
FR1, FR2, FR3 and FR4 are each framework regions;
CDR1, CDR2 and CDR3 are each complementarity determining regions;
FR1a, FR2a, FR3a and FR4a are each framework regions;
CDR1a, CDR2a and CDR3a are each complementarity determining regions;
wherein the sequence of any of the complementarity determining regions have an amino acid sequence as described in Table 1 below. Preferably, the framework regions have an amino acid sequence also as described in Table 1 below, including amino acid variation at particular residues which can be determined by aligning the various framework regions derived from each antibody. The invention also includes where CDR1, CDR2 and CDR3 are sequences from the VH, CDR1a, CDR2a and CDR3a are sequences from VL, or where CDR1, CDR2 and CDR3 are sequences from the VL, CDR1a, CDR2a and CDR3a are sequences from VH.

The present invention also provides an antigen binding protein that binds to or specifically binds to plasmin and wherein the antigen binding protein competitively inhibits binding of the B10 antibody (i.e., comprising: a VH comprising a sequence set forth in SEQ ID NO: 8 and a VL comprising a sequence set forth in SEQ ID NO: 7) to plasmin.

The invention provides an antigen binding protein for binding to plasmin, the antigen binding protein including:
FR1-CDR1-FR2-CDR2-FR3-CDR3-FR4-linker-FR1a-CDR1a-FR2a-CDR2a-FR3a-CDR3a-FR4a
wherein:
FR1, FR2, FR3 and FR4 are each framework regions;
CDR1, CDR2 and CDR3 are each complementarity determining regions;
FR1a, FR2a, FR3a and FR4a are each framework regions;
CDR1a, CDR2a and CDR3a are each complementarity determining regions;
As defined herein, the linker may be a chemical, one or more amino acids, or a disulphide bond formed between two cysteine residues.

The invention provides an antigen binding protein comprising, consisting essentially of or consisting of an amino acid sequence of (in order of N to C terminus or C to N terminus) SEQ ID NO: 7 and 8.

The present invention also provides an antigen binding protein comprising an antigen binding domain of an antibody, wherein the antigen binding domain binds to or specifically binds to plasmin, wherein the antigen binding domain comprises at least one of:

(i) a VH comprising a complementarity determining region (CDR) 1 comprising a sequence at least about 80%, at least 85%, at least 90%, at least 92%, at least 95%, at least 97%, at least 99% identical to a sequence set forth in SEQ ID NO:4, a CDR2 comprising a sequence at least about 80%, at least 85%, at least 90%, at least 92%, at least 95%, at least 97%, at least 99% identical to a sequence set in SEQ ID NO:5 and a CDR3 comprising a sequence at least about 80%, at least 85%, at least 90%, at least 92%, at least 95%, at least 97%, at least 99% identical to a sequence set forth in SEQ ID NO: 6;

(ii) a VH comprising a sequence at least about 95% or 96% or 97% or 98% or 99% identical to a sequence set forth in SEQ ID NO: 8;

(iii) a VL comprising a CDR1 comprising a sequence at least about 80%, at least 85%, at least 90%, at least 92%, at least 95%, at least 97%, at least 99% identical to a sequence set forth in SEQ ID NO: 1, a CDR2 comprising a sequence at least about 80%, at least 85%, at least 90%, at least 92%, at least 95%, at least 97%, at least 99% identical to a sequence set forth in SEQ ID NO: 2 and a CDR3 comprising a sequence at least about 80%, at least 85%, at least 90%, at least 92%, at least 95%, at least 97%, at least 99% identical to a sequence set forth in SEQ ID NO: 3;

(iv) a VL comprising a sequence at least about 95% identical to a sequence set forth in SEQ ID NO: 7;

(v) a VH comprising a CDR1 comprising a sequence set forth in SEQ ID NO: 4, a CDR2 comprising a sequence set forth between in SEQ ID NO: 5 and a CDR3 comprising a sequence set forth in SEQ ID NO: 6;

(vi) a VH comprising a sequence set forth in SEQ ID NO: 8;

(vii) a VL comprising a CDR1 comprising a sequence set SEQ ID NO: 1, a CDR2 comprising a sequence set forth in SEQ ID NO: 2 and a CDR3 comprising a sequence set forth in SEQ ID NO: 3;

(viii) a VL comprising a sequence set forth in SEQ ID NO: 7;

(ix) a VH comprising a CDR1 comprising a sequence set forth in SEQ ID NO: 4, a CDR2 comprising a sequence set forth between in SEQ ID NO: 5 and a CDR3 comprising a sequence set forth in SEQ ID NO: 6; and a VL comprising a CDR1 comprising a sequence set SEQ ID NO: 1, a CDR2 comprising a sequence set forth in SEQ ID NO: 2 and a CDR3 comprising a sequence set forth in SEQ ID NO: 3; or (x) a VH comprising a sequence setforth in SEQ ID NO: 8 and a VL comprising a sequence set forth in SEQ ID NO: 7.

In any aspect of the invention, the antigen binding domain further comprises at least one of:

(i) a VH comprising a framework region (FR) 1 comprising a sequence at least about 80%, at least 85%, at least 90%, at least 92%, at least 95%, at least 97%, at least 99% identical to a sequence set forth in SEQ ID NO:21, a FR2 comprising a sequence at least about 80%, at least 85%, at least 90%, at least 92%, at least 95%, at least 97%, at least 99% identical to a sequence set in SEQ ID NO:22, a FR3 comprising a sequence at least about 80%, at least 85%, at least 90%, at least 92%, at least 95%, at least 97%, at least 99% identical to a sequence set forth in SEQ ID NO: 23, and a FR4 comprising a sequence at least about 80%, at least 85%, at least 90%, at least 92%, at least 95%, at least 97%, at least 99% identical to a sequence set forth in SEQ ID NO: 24;

(ii) a VL comprising a FR1 comprising a sequence at least about 80%, at least 85%, at least 90%, at least 92%, at least 95%, at least 97%, at least 99% identical to a sequence set forth in SEQ ID NO: 17, a FR2 comprising a sequence at least about 80%, at least 85%, at least 90%, at least 92%, at least 95%, at least 97%, at least 99% identical to a sequence set forth in SEQ ID NO: 18, a FR3 comprising a sequence at least about 80%, at least 85%, at least 90%, at least 92%, at least 95%, at least 97%, at least 99% identical to a sequence set forth in SEQ ID NO: 19, and a FR4 comprising a sequence at least about 80%, at least 85%, at least 90%, at least 92%, at least 95%, at least 97%, at least 99% identical to a sequence set forth in SEQ ID NO: 20;

(iii) a VH comprising a FR1 comprising a sequence set forth in SEQ ID NO: 21, a FR2 comprising a sequence set forth between in SEQ ID NO: 22, a FR3 comprising a sequence setforth in SEQ ID NO: 23, and a FR4 comprising a sequence set forth in SEQ ID NO: 24;

(iv) a VL comprising a FR1 comprising a sequence set forth in SEQ ID NO: 17, a FR2 comprising a sequence set forth between in SEQ ID NO: 18, a FR3 comprising a sequence set forth in SEQ ID NO: 19, and a FR4 comprising a sequence set forth in SEQ ID NO: 20; or (v) a VH comprising a FR1 comprising a sequence set forth in SEQ ID NO: 21, a FR2 comprising a sequence set forth between in SEQ ID NO: 22, a FR3 comprising a sequence set forth in SEQ ID NO: 23, and a FR4 comprising a sequence set forth in SEQ ID NO: 24; and a VL comprising a FR1 comprising a sequence set forth in SEQ ID NO: 17, a FR2 comprising a sequence set forth between in SEQ ID NO: 18, a FR3 comprising a sequence set forth in SEQ ID NO: 19, and a FR4 comprising a sequence set forth in SEQ ID NO: 20.

As described herein, the antigen binding protein may be in the form of:

(i) a single chain Fv fragment (scFv);

(ii) a dimeric scFv (di-scFv);

(iii) one of (i) or (ii) linked to a constant region of an antibody, Fc or a heavy chain constant domain (CH) 2 and/or CH3; or (iv) one of (i) or (ii) linked to a protein that binds to an immune effector cell.

Further, as described herein, the antigen binding protein may be in the form of:

(i) a diabody;

(ii) a triabody;

(iii) a tetrabody;

(iv) a Fab;

(v) a F(ab')2;

(vi) a Fv;

(vii) a bispecific antibody or other form of multispecific antibody;

(viii) one of (i) to (vii) linked to a constant region of an antibody, Fc or a heavy chain constant domain (CH) 2 and/or CH3; or (viv) one of (i) to (vii) linked to a protein that binds to an immune effector cell.

The foregoing antigen binding proteins can also be referred to as antigen binding domains of antibodies.

Preferably, an antigen binding protein as described herein is an antibody or antigen binding fragment thereof. Typically, the antigen binding protein is an antibody, for example, a monoclonal antibody. The antigen binding protein may be in the form of a recombinant or modified antibody (e.g., chimeric antibody, humanized antibody, human antibody, CDR-grafted antibody, primatized antibody, de-immunized antibody, synhumanized antibody, half-antibody, bispecific antibody, trispecific antibody or multi-specific antibody). The antibody may further comprise a chemical modification, such as conjugation to an active agent or radiolabel, or an agent for improving solubility or other modification described herein.

As used herein the antigen binding protein may be a variable domain.

The present invention also provides an anti-plasmin antibody comprising a light chain variable region and a heavy chain variable region, wherein said light chain variable region comprises:

a CDR L1 as set forth in SEQ ID NO: 1, a CDR L2 as set forth in SEQ ID NO: 2 and a CDR L3 as set forth in SEQ ID NO: 3; and wherein said heavy chain variable region comprises:

a CDR H1 as set forth in SEQ ID NO: 4, a CDR H2 as set forth in SEQ ID NO: 5, and a CDR H3 as set forth in SEQ ID NO: 6.

In any aspect of the invention, an anti-plasmin antibody comprises a light chain variable region that comprises the sequence of SEQ ID NO: 7.

In any aspect of the invention, an anti-plasmin antibody comprises a heavy chain variable region that comprises the sequence of SEQ ID NO: 8.

In any aspect of the invention, an anti-plasmin antibody comprises a light chain variable region that comprises a FR L1 as set forth in SEQ ID NO: 17, FR L2 as set forth in SEQ ID NO: 18, a FR L3 as set forth in SEQ ID NO: 19 and a FR L4 as set forth in SEQ ID NO: 20.

In any aspect of the invention, an anti-plasmin antibody comprises a heavy chain variable region that comprises a FR H1 as set forth in SEQ ID NO: 21, FR H2 as set forth in SEQ ID NO: 22, a FR H3 as set forth in SEQ ID NO: 23 and a FR H4 as set forth in SEQ ID NO: 24.

In any aspect of the present invention, the antibody is a naked antibody. Specifically, the antibody is in a non-conjugated form and is not adapted to form a conjugate.

In certain embodiments, the complementarity determining region sequences (CDRs) of an antigen binding protein of the invention may be defined according to the IMGT numbering system.

Reference herein to a protein or antibody that "binds to" plasmin provides literal support for a protein or antibody that "binds specifically to" or "specifically binds to" plasmin.

The present invention also provides antigen binding domains or antigen binding fragments of the foregoing antibodies.

The invention also provides a fusion protein comprising an antigen binding protein, immunoglobulin variable domain, antibody, dab (single domain antibody), di-scFv, scFv, Fab, Fab', F(ab')2, Fv fragment, diabody, triabody, tetrabody, linear antibody, single-chain antibody molecule, or multispecific antibody as described herein.

The invention also provides a conjugate in the form of an antigen binding protein, immunoglobulin variable domain, antibody, dab, di-scFv, scFv, Fab, Fab', F(ab')2, Fv fragment, diabody, triabody, tetrabody, linear antibody, single-chain antibody molecule, or multispecific antibody or fusion protein as described herein conjugated to a label or a cytotoxic agent.

The invention also provides an antibody for binding to an antigen binding protein, immunoglobulin variable domain, antibody, dab, di-scFv, scFv, Fab, Fab', F(ab')2, Fv fragment, diabody, triabody, tetrabody, linear antibody, single-chain antibody molecule, or multispecific antibody (e.g., a bi-specific antibody or tri-specific antibody), fusion protein, or conjugate as described herein.

The invention also provides a nucleic acid encoding an antigen binding protein, immunoglobulin variable domain, antibody, dab, di-scFv, scFv, Fab, Fab', F(ab')2, Fv fragment, diabody, triabody, tetrabody, linear antibody, single-chain antibody molecule, or multispecific antibody, fusion protein or conjugate as described herein.

In one example, such a nucleic acid is included in an expression construct in which the nucleic acid is operably linked to a promoter. Such an expression construct can be in a vector, e.g., a plasmid.

In examples of the invention directed to single polypeptide chain antigen binding protein, the expression construct may comprise a promoter linked to a nucleic acid encoding that polypeptide chain.

In examples directed to multiple polypeptide chains that form an antigen binding protein, an expression construct comprises a nucleic acid encoding a polypeptide comprising, e.g., a VH operably linked to a promoter and a nucleic acid encoding a polypeptide comprising, e.g., a VL operably linked to a promoter.

In another example, the expression construct is a bicistronic expression construct, e.g., comprising the following operably linked components in 5' to 3' order:
(i) a promoter
(ii) a nucleic acid encoding a first polypeptide;
(iii) an internal ribosome entry site; and
(iv) a nucleic acid encoding a second polypeptide,

wherein the first polypeptide comprises a VH and the second polypeptide comprises a VL, or vice versa.

The present invention also contemplates separate expression constructs one of which encodes a first polypeptide comprising a VH and another of which encodes a second polypeptide comprising a VL. For example, the present invention also provides a composition comprising:
(i) a first expression construct comprising a nucleic acid encoding a polypeptide comprising a VH operably linked to a promoter; and
(ii) a second expression construct comprising a nucleic acid encoding a polypeptide comprising a VL operably linked to a promoter.

The invention provides a cell comprising a vector or nucleic acid described herein. Preferably, the cell is isolated, substantially purified or recombinant. In one example, the cell comprises the expression construct of the invention or:
(i) a first expression construct comprising a nucleic acid encoding a polypeptide comprising a VH operably linked to a promoter; and
(ii) a second expression construct comprising a nucleic acid encoding a polypeptide comprising a VL operably linked to a promoter, wherein the first and second polypeptides associate to form an antigen binding protein of the present invention.

Examples of cells of the present invention include bacterial cells, yeast cells, insect cells or mammalian cells.

The invention also provides a pharmaceutical composition comprising an antigen binding protein, or comprising a CDR and/or FR sequence as described herein, or an immunoglobulin variable domain, antibody, dab (single domain antibody), di-scFv, scFv, Fab, Fab', F(ab')2, Fv fragment, diabody, triabody, tetrabody, linear antibody, single-chain antibody molecule, or multispecific antibody, fusion protein, or conjugate as described herein and a pharmaceutically acceptable carrier, diluent or excipient.

The invention also provides a diagnostic composition comprising an antigen binding protein, or comprising a CDR and/or FR sequence as described herein, or antigen binding site, immunoglobulin variable domain, antibody, dab, di-scFv, scFv, Fab, Fab', F(ab')2, Fv fragment, diabody, tetrabody, linear antibody, single-chain antibody molecule, or multispecific antibody, fusion protein or conjugate as described herein, a diluent and optionally a label.

The invention also provides a kit or article of manufacture comprising an antigen binding protein, or comprising a CDR and/or FR sequence as described herein or an immunoglobulin variable domain, antibody, dab, di-scFv, scFv, Fab, Fab', F(ab')2, Fv fragment, diabody, triabody, tetrabody, linear antibody, single-chain antibody molecule, or multispecific antibody, fusion protein or conjugate as described herein.

An antigen binding protein as described herein may comprise a human constant region, e.g., an IgG constant region, such as an IgG1, IgG2, IgG3 or IgG4 constant region or mixtures thereof. In the case of an antibody or protein comprising a VH and a VL, the VH can be linked to a heavy chain constant region and the VL can be linked to a light chain constant region.

In one example, an antigen binding protein as described herein comprises a constant region of an IgG4 antibody or a stabilized constant region of an IgG4 antibody. In one example, the protein or antibody comprises an IgG4 constant region with a proline at position 241 (according to the numbering system of Kabat (Kabat et al., Sequences of Proteins of Immunological Interest Washington D.C. United States Department of Health and Human Services, 1987 and/or 1991)).

In one example, an antigen binding protein as described herein or a composition of an antigen binding protein as described herein, comprises a heavy chain constant region, comprising a stabilized heavy chain constant region, comprising a mixture of sequences fully or partially with or without the C-terminal lysine residue.

In one example, an antigen binding protein comprises a VH disclosed herein linked or fused to an IgG4 constant region or stabilized IgG4 constant region (e.g., as discussed above) and the VL is linked to or fused to a kappa light chain constant region.

The functional characteristics of an antigen binding protein of the invention will be taken to apply mutatis mutandis to an antibody of the invention.

An antigen binding protein as described herein may be purified, substantially purified, isolated and/or recombinant.

An antigen binding protein of the invention may be part of a supernatant taken from media in which a hybridoma expressing an antigen binding protein of the invention has been grown.

The present invention provides a method of inhibiting plasmin activity in a subject in need thereof comprising administering to the subject a plasmin-inhibiting antigen binding protein of the invention, thereby inhibiting plasmin activity in the subject. A subject in need may include a subject suffering from haemophilia, menorrhagia, von Willebrand syndrome or thrombolytic-induced bleeding.

Preferably, inhibiting plasmin activity includes inhibiting plasmin cleavage of one or more substrates of plasmin selected from the group consisting of: fibrin, fibrinogen, Factors V, VIII and X, protease-activated receptor I, fibronectin, thrombospondin, laminin, von Willebrand factor, vitronectin, pro-brain-derived neurotrophic factor, complement C3 and C5, tenascin, osteocalin, CUB domain-containing protein 1 and other proteases such as collagenase.

The present invention provides a method of inhibiting fibrinolysis in a subject in need thereof, the method comprising administering an antigen binding protein of the invention to the subject, thereby inhibiting fibrinolysis in the subject.

The present invention also provides a method of restoring haemostasis or for inhibiting plasmin activity in a subject who has suffered a trauma or who is has suffered a haemorrhage or is haemorrhaging (for example, due to surgery, trauma or following child-birth), the method comprising administering an antigen binding protein of the invention to the subject, thereby restoring haemostasis or for inhibiting plasmin activity in the subject.

The present invention also provides a method of treating or preventing a Streptococcal infection in a subject, the method comprising administering an antigen binding protein of the invention to the subject, thereby treating or preventing the Streptococcal infection in the subject. In this regard, an antigen binding protein can be used to prevent a relapse of an infection, and this is considered preventing the infection.

The present invention provides a method of inhibiting fibrinolysis in a subject in need thereof, the method comprising administering an antigen binding protein of the invention to the subject, thereby inhibiting fibrinolysis in the subject.

The invention also provides a method for treating a condition associated with, or caused by, a Streptococcal infection in a subject, the method comprising administering to the subject an effective amount of the antigen binding protein of the invention, thereby treating the condition associated with, or caused by, a Streptococcal infection in the subject. A condition associated with, or caused by, a Streptococcal infection may be any condition described herein. In any aspect of the invention, the Streptococcal infection may be chronic or acute.

The present invention also provides a method of reducing the severity of a Streptococcal infection in a subject, the method the method comprising administering an antigen binding protein of the invention to the subject, thereby reducing the severity of the Streptococcal infection in the subject.

Still further, the invention provides for a method of treating or preventing a cancer in a subject, the method comprising administering an antigen binding protein of the invention to the subject, thereby treating or preventing a cancer in the subject. As used herein, methods of treating cancer include methods of inhibiting, preventing or minimising spread or progression of a cancer, including inhibiting or preventing metastasis of cancer.

The present invention provides for the use of an antigen binding protein of the invention, in the manufacture of a medicament for inhibiting plasmin activity in a subject in need thereof, including for inhibiting plasmin activity in a subject suffering from haemophilia, menorrhagia, von Willebrand syndrome or thrombolytic-induced bleeding.

The present invention also provides for the use of an antigen binding protein of the invention, in the manufacture of a medicament for the restoration of haemostasis or inhibition of excessive plasmin activity in a subject who has suffered a trauma, or requires restoration of haemostasis or inhibition of plasmin activity following surgery or childbirth.

The present invention also provides for the use of an antigen binding protein of the invention, in the manufacture of a medicament for the restoration or haemostasis or inhibition of excessive plasmin activity in a subject who has suffered a trauma.

The present invention provides for the use of an antigen-binding protein of the invention in the manufacture of a medicament for inhibiting fibrinolysis in a subject in need thereof.

The present invention also provides for the use of an antigen binding protein of the invention, in the manufacture of a medicament for the treatment or prevention of a Streptococcal infection.

The present invention also provides for the use of an antigen binding protein of the invention, in the manufacture of a medicament for the treatment, prevention or reduction in severity of any condition or disease that is caused by or associated with a Streptococcal infection.

Still further, the invention provides for use of an antigen binding protein of the invention in the manufacture of a medicament for treating or preventing a cancer in a subject. The medicament may also be for inhibiting, preventing or minimising spread or progression of a cancer, including metastasis of a cancer.

The invention also provides for a pharmaceutical composition comprising an antigen binding protein of the invention, and a pharmaceutically acceptable excipient.

The pharmaceutical composition is preferably for a use as recited herein. Accordingly the invention provides a pharmaceutical composition comprising an antigen binding protein of the invention, for use in inhibiting plasmin activity in a subject in need thereof, including for inhibiting plasmin activity in a subject suffering from haemophilia, menorrhagia, von Willebrand syndrome or thrombolytic-induced bleeding.

The present invention also provides a pharmaceutical composition for use in the restoration of haemostasis or inhibition of excessive plasmin activity in a subject who has suffered a trauma, or requires restoration of haemostasis or inhibition of plasmin activity following surgery or childbirth.

The present invention also provides a pharmaceutical composition comprising an antigen binding protein of the invention, for use in the restoration or haemostasis or inhibition of excessive plasmin activity in a subject who has suffered a trauma.

The present invention also provides a pharmaceutical composition comprising an antigen binding protein of the invention for use in the treatment or prevention of a Streptococcal infection.

The present invention also provides a pharmaceutical composition comprising an antigen binding protein of the invention for use in the treatment, prevention or reduction in severity of any condition or disease that is caused by or associated with a Streptococcal infection.

Further, the invention provides for a pharmaceutical composition comprising an antigen binding protein of the invention for use in treating or preventing a cancer in a subject. The pharmaceutical composition may also be for inhibiting, preventing or minimising spread or progression of a cancer, including metastasis of a cancer.

In any aspect of the invention, the Streptococcal infection is caused by bacteria from the family Streptococcaceae. Preferably the bacteria are from the genus *Streptococcus*. More preferably, the bacteria are Group A *streptococcus* (GAS), preferably *Streptococcus pyogenes*. In certain aspects of the invention, the infection may be an infection caused by the bacteria selected from the group consisting of: *Streptococcus pyogenes, Streptococcus dysgalactiae* and *Streptococcus pneumonia*.

Accordingly, a method, use or pharmaceutical composition of the invention is useful in the treatment, prevention or reduction in severity of any disease that is caused by or associated with a bacterium referred to herein. For example, a method, use or pharmaceutical composition of the invention may be for treating, preventing or reducing the severity of any disease/infection caused by or associated with a Group A *Streptococcus* (GAS), including, but not limited to, pharyngitis, tonsillitis, scarlet fever, cellulitis, erysipelas, rheumatic fever, skin and soft-tissue infection, endocarditis, bone and joint infections, infected implants, post-streptococcal glomerulonephritis, necrotizing fasciitis, myonecrosis subperiosteal abscesses, necrotizing pneumonia, pyomyositis, mediastinitis, myocardial, perinephric, hepatic, and splenic abscesses, septic thrombophlebitis, and severe ocular infections, including endophthalmitis and lymphangitis.

The methods and uses of the invention are applicable to the treatment or prevention of a cancer. Exemplary cancers include haematologic cancers, cancers of epithelial origin, liver cancer, pancreatic cancer, gastric cancer, osteosarcoma, endometrial cancer and ovarian cancer.

The present invention further provides a nucleic acid molecule encoding an antigen binding protein of the invention, or functional fragment or derivative thereof.

The invention also provides a cell comprising a vector or nucleic acid molecule described herein.

The invention also provides an animal or tissue derived therefrom comprising a cell described herein.

In another aspect the present invention provides a kit or article of manufacture including an antigen binding protein of the invention or pharmaceutical composition of the invention as described herein.

In other aspects of the invention there is provided a kit for use in a therapeutic or prophylactic application mentioned herein, the kit including:

a container holding an antigen binding protein or pharmaceutical composition of the invention; and a label or package insert with instructions for use.

As used herein, except where the context requires otherwise, the term "comprise" and variations of the term, such as "comprising", "comprises" and "comprised", are not intended to exclude further additives, components, integers or steps.

Further aspects of the present invention and further embodiments of the aspects described in the preceding paragraphs will become apparent from the following description, given by way of example and with reference to the accompanying drawings.

BRIEF DESCRIPTION OF THE DRAWINGS

FIG. 1: Binding of B10 binds to plasminogen and plasmin. B10 was immobilised on a NiHc chip; binding kinetics of B10 (A) Plasminogen and (B) Plasmin was measured by multi-cycle surface plasmon resonance (SPR), dotted lines represent 1:1 Langmuir model fit to experimental data; (C) a summary table for the kinetic (ka and $k_d$) and affinity constants ($K_D$).

FIG. 2: Dose-dependent inhibition of tPA-mediated plasminogen activation by B10. B10 inhibits activity of plasmin generated by tPA-mediated plasminogen activation (A) in the presence of EACA in solution, or (B) on fibrin clot.

FIG. 5: Inhibition of streptokinase binding to plasminogen by B10. (A) 10 nM plasminogen was passed over streptokinase which is immobilized on a CM4 chip in the presence of B10 or a naïve chicken AB, gAb (at 0-500 nM). B10 showed inhibition at concentrations 62.5-500 nM. Naïve chicken antibody gAb, the control, showed no inhibition of Plg binding to SK. (B) Percentage of plasminogen binding to SK in the presence of 500 nM Abs, normalized against no antibody control.

FIG. 7: Crystal structure of B10 bound to the serine protease domains of plasmin (SP). The crystal structure of SP/B10 binary complex shows that B10 binds to the plasmin catalytic triad. SP is shown, the catalytic triad is shown in sticks and labelled, B10 light chain (LC) and heavy chain (HC) are labelled. At the top is the cartoon representation of the binary complex and the bottom shows the key residues, labelled and numbered, involved in intermolecular interactions and labelled as above. Dashed lines are used to illustrate polar interactions.

FIG. 8: B10 inhibits plasmin generation by Group A *Streptococcus* (GAS) (enzyme assay). (Top) Plasminogen bound to B10 was incubated with GAS. Activity of plasmin generated was measured with the fluorogenic substrate. Here plasmin generation by GAS is expected to be mediated by streptokinase (SK). (Bottom) Progression curve of plasmin activity in the presence or absence of recombinant SK.

DETAILED DESCRIPTION OF THE EMBODIMENTS

Figure 3:
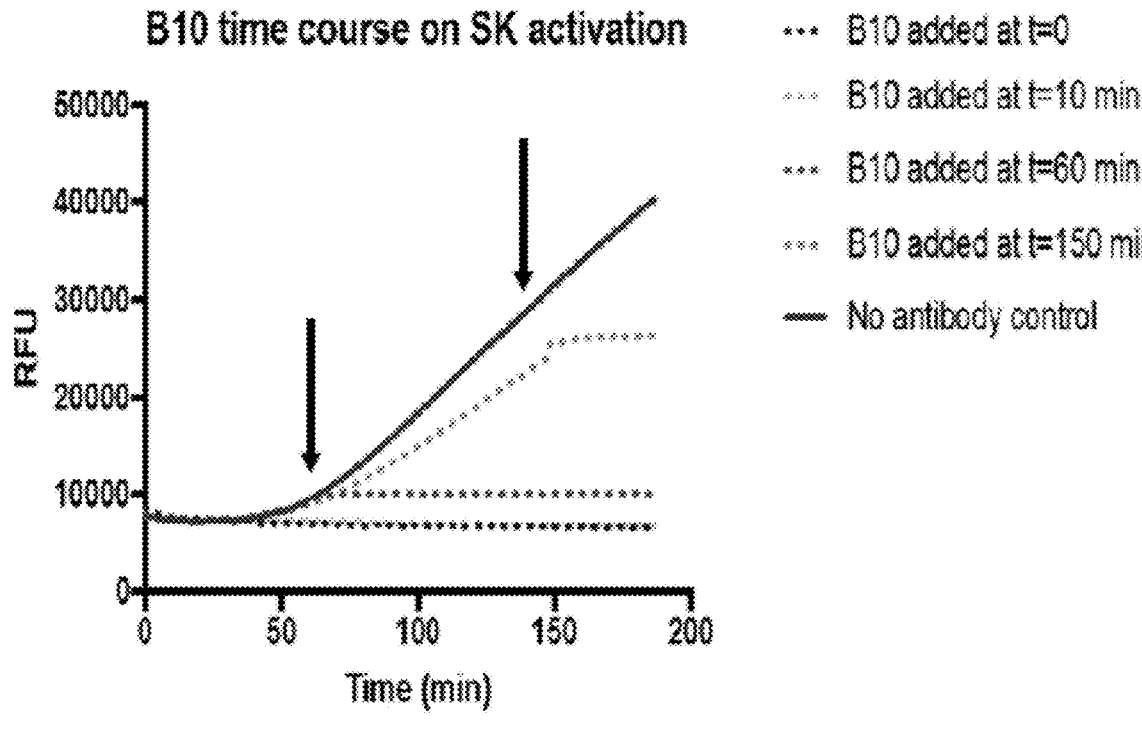
FIG. 3: Inhibition of SK-mediated plasminogen activation by B10. B10 instantaneously inhibits plasmin activity as it is added to the reaction (at a 20-fold molar excess) at any time during the entire course of the assay. This result indicates that B10 inhibits plasmin activity.

It will be understood that the invention disclosed and defined in this specification extends to all alternative combinations of two or more of the individual features mentioned or evident from the text or drawings. All of these different combinations constitute various alternative aspects of the invention.

Further aspects of the present invention and further embodiments of the aspects described in the preceding paragraphs will become apparent from the following description, given by way of example and with reference to the accompanying drawings.

Reference will now be made in detail to certain embodiments of the invention. While the invention will be described in conjunction with the embodiments, it will be understood that the intention is not to limit the invention to those embodiments. On the contrary, the invention is intended to coverall alternatives, modifications, and equivalents, which may be included within the scope of the present invention as defined by the claims.

Haemorrhage, or bleeding, is a serious or fatal complication of surgery, injury or coagulation factor deficiency. Antifibrinolytic agents that inhibit plasmin-mediated fibrinolysis or clot dissolution may reduce blood loss, emergency reoperation, morbidity and death in severe haemorrhage.

Unchecked plasmin dissolves thrombi (fibrinolysis) and degrades clotting factors (fibrinogen, factor V, factor VIII), which impairs coagulation, thereby enhancing bleeding risk. In addition, unchecked plasmin activates neutrophils and macrophages, increasing chemotaxis and oxidative stress, as well as promoting release of pro-inflammatory cytokines and matrix metalloproteinases.

Since their first use more than 50 years ago, small molecule plasmin inhibitors have been shown to reduce bleeding and associated complications. Currently available plasmin inhibitors are typically in the form of small molecules that block the enzyme active site or interfere with the interactions of plasmin with substrates.

The lysine analogs, epsilon amino caproic acid (EACA) and tranexamic acid (TX), simulate lysine residues and interact with lysine binding sites on plasmin kringles to block its interactions with fibrin. Due to their molecular size and mechanism of action, lysine analogs have low potency and modest specificity, they accumulate in kidney disease and penetrate the blood brain barrier and placenta. Lysine analogs prevent plasminogen and tPA from binding to fibrin, thereby inhibiting plasminogen activation and fibrinolysis. Through the same mechanisms, lysine analogs may actually increase plasmin activity by blocking kringle interactions with a2-antiplasmin and by enhancing plasminogen activation by tPA or uPA in solution. Lysine analogs also interfere with the interactions of plasminogen-plasmin with cellular receptors and block interactions of plasminogen with tissue factor. The biological effects of the interactions of the lysine analogs with other kringle-containing proteins (tPA, (pro) thrombin, hepatocyte growth factors, uPA, apoprotein (a) of lipoprotein(a)), are not well understood. Lysine analogs cross the placenta and the blood brain barrier, cause seizures in cardiac surgical patients and increase brain infarction in subarachnoid hemorrhage patients.

Major clinical trials have been aimed at understanding the efficacy of small molecule plasminogen activation inhibitors in inhibiting fibrinolysis and restoring haemostasis in trauma. These studies have revealed that small molecule plasmin inhibitors are limited by non-specific mechanisms of action, off-target effects, low potency and lack of efficacy for certain types of haemorrhage. In particular, the CRASH-2 and MATTERs trials investigated the efficacy of the lysine analog tranexamic acid (TXA) and revealed that administration of TXA to patients with severe within 3 hours of injury significantly reduced mortality. Importantly, the studies also revealed that the survival benefit of TXA decreased by 10% for every 15 minutes of delayed administration, with no benefit obtained after 3 hours. It is thought that this is due to a change of the coagulation and fibrinolytic proteome in vivo, leading to an increase in uPA-mediated plasminogen activation to plasmin. Thus, plasmin generated in plasma leads to an increase in non-specific fibrinolytic potential resulting from the degradation of fibrinogen and depletion of alpha2-antiplasmin. Thus, there is also a need for a plasmin active site inhibitor for use in clinical situations where inhibition of plasminogen activation is no longer useful.

There is a need for fibrinolytic inhibitors with greater specificity and potency, particularly in patients with serious, life-threatening haemorrhage, such as brain bleeding where current therapies are ineffective and may be harmful, in part because of off-target effects. Creating highly specific catalytic inhibitors of plasmin is challenging, because its enzymatic active site has significant homology with other trypsin-like serine proteases. For example, the most commonly used plasmin active site inhibitor is aprotinin. However, this molecule is a non-specific inhibitor of numerous other serine proteases including trypsin, thrombin, activated protein C, kallikrein, neutrophil elastase and other proteases. Aprotinin is no longer available for use in the US due to safety concerns associated with increased mortality. Thus, there is a need for a plasmin-specific inhibitor, which has minimal inhibitor activity against other serine proteases.

The present inventors have developed antigen binding proteins, for example antibodies, that bind to and inhibit or reduce the catalytic activity of plasmin.

The antigen binding proteins of the invention have been demonstrated to bind specifically to the serine protease domain of plasmin, and to inhibit plasmin activity via interactions with the catalytic site of the protein.

Advantageously, the antigen binding proteins of the invention do not inhibit the activity of other serine proteases, including tPA, thombin, trypsin, Factor Xa ad plasma kallikrein.

By virtue of their ability to bind to and inhibit or reduce plasmin activity, and as further explained herein, the antigen binding proteins of the invention are useful for treating, preventing or delaying the progression of conditions or diseases mediated by plasmin and the fibrinolytic system. For example, the antigen binding proteins of the invention are useful for promoting haemostasis following trauma, or haemorrhage following surgery or child-birth.

The antigen binding proteins of the invention also have utility for treating or preventing bacterial infections where the bacteria utilises Streptokinase, or a related enzyme, in order to recruit the plasmin system to promote invasion of host tissues. In particular, the antigen binding proteins of the invention are useful for treating or preventing infections caused by *Streptococcus* sp.

The plasmin system can also be employed by invading tumours to promote angiogenesis and metastasis. Accordingly, the antigen binding proteins of the invention also have the capacity to inhibit or reduce one or more aspects of the inflammatory, tumour growth and metastatic activity.

General

Throughout this specification, unless specifically stated otherwise or the context requires otherwise, reference to a single step, composition of matter, group of steps or group of compositions of matter shall be taken to encompass one and a plurality (i.e. one or more) of those steps, compositions of matter, groups of steps or groups of compositions of matter. Thus, as used herein, the singular forms "a", "an" and "the" include plural aspects, and vice versa, unless the context clearly dictates otherwise. For example, reference to "a" includes a single as well as two or more; reference to "an" includes a single as well as two or more; reference to "the" includes a single as well as two or more and so forth.

Those skilled in the art will appreciate that the present invention is susceptible to variations and modifications other than those specifically described. It is to be understood that the invention includes all such variations and modifications. The invention also includes all of the steps, features, compositions and compounds referred to or indicated in this specification, individually or collectively, and any and all combinations or any two or more of said steps or features.

One skilled in the art will recognize many methods and materials similar or equivalent to those described herein, which could be used in the practice of the present invention. The present invention is in no way limited to the methods and materials described.

All of the patents and publications referred to herein are incorporated by reference in their entirety.

The present invention is not to be limited in scope by the specific examples described herein, which are intended for the purpose of exemplification only. Functionally-equivalent products, compositions and methods are clearly within the scope of the present invention.

Any example or embodiment of the present invention herein shall be taken to apply mutatis mutandis to any other example or embodiment of the invention unless specifically stated otherwise.

Unless specifically defined otherwise, all technical and scientific terms used herein shall be taken to have the same meaning as commonly understood by one of ordinary skill in the art (for example, in cell culture, molecular genetics, immunology, immunohistochemistry, protein chemistry, and biochemistry).

Unless otherwise indicated, the recombinant protein, cell culture, and immunological techniques utilized in the present disclosure are standard procedures, well known to those skilled in the art. Such techniques are described and explained throughout the literature in sources such as, J. Perbal, A Practical Guide to Molecular Cloning, John Wiley and Sons (1984), J. Sambrook et al. Molecular Cloning: A Laboratory Manual, Cold Spring Harbour Laboratory Press (1989), T. A. Brown (editor), Essential Molecular Biology: A Practical Approach, Volumes 1 and 2, IRL Press (1991), D. M. Glover and B. D. Hames (editors), DNA Cloning: A Practical Approach, Volumes 1-4, IRL Press (1995 and 1996), and F. M. Ausubel et al. (editors), Current Protocols in Molecular Biology, Greene Pub. Associates and Wiley-Interscience (1988, including all updates until present), Ed Harlow and David Lane (editors) Antibodies: A Laboratory Manual, Cold Spring Harbour Laboratory, (1988), and J. E. Coligan et al. (editors) Current Protocols in Immunology, John Wiley & Sons (including all updates until present).

The description and definitions of variable regions and parts thereof, immunoglobulins, antibodies and fragments thereof herein may be further clarified by the discussion in Kabat Sequences of Proteins of Immunological Interest, National Institutes of Health, Bethesda, Md., 1987 and 1991, Bork et al., J Mol. Biol. 242, 309-320, 1994, Chothia and Lesk J. Mol Biol. 196:901-917, 1987, Chothia et al. Nature 342, 877-883, 1989 and/or or AI-Lazikani et al., J Mol Biol 273, 927-948, 1997.

The term "and/or", e.g., "X and/or Y" shall be understood to mean either "X and Y" or "X or Y" and shall be taken to provide explicit support for both meanings or for either meaning.

As used herein the term "derived from" shall be taken to indicate that a specified integer may be obtained from a particular source albeit not necessarily directly from that source.

Reference herein to a range of, e.g., residues, will be understood to be inclusive. For example, reference to "a region comprising amino acids 56 to 65" will be understood in an inclusive manner, i.e., the region comprises a sequence of amino acids as numbered 56, 57, 58, 59, 60, 61, 62, 63, 64 and 65 in a specified sequence.

Selected Definitions

Plasmin plays an important role in cell migration, tissue remodeling, and bacterial invasion. Plasmin is a serine protease that preferentially cleaves Lys-Xaa and Arg-Xaa bonds with higher selectivity than trypsin. Plasmin is the active form of the zymogen plasminogen. Plasminogen is activated to plasmin by the proteolytic action of various activators on plasminogen. Plasminogen activators such as tissue plasminogen activator (tPA) or urokinase (uPa) cleave the human plasminogen molecule at the $Arg_{561}$-$Val_{562}$ bond to produce active plasmin. The two resulting chains of plasmin are held together by two interchain disulphide bridges. The light chain (25 kDa) carries the catalytic center (which comprises the catalytic triad) and shares sequence similarity with trypsin and other serine proteases. The heavy chain (60 kDa) consists of five highly similar triple-loop structures called kringles. Some of the kringles contain lysine binding sites that mediates the plasminogen/plasmin interaction with fibrin. Plasmin belongs to peptidase family Si.

Plasmin (or Plm) is a seven-domain glycoprotein comprising a Pap or pan-apple domain, 5 kringle domains (KR 1 to KR5) and a serine protease (SP) domain. The inactive form, plasminogen (Plg) circulates in a closed and activation-resistant conformation in plasma. Upon localization to a target site, plasminogen binds to the surface lysine/arginine residues on the targets (which include fibrin clots and cell surface receptors). Binding occurs via lysine-binding sites (LBSs) on the kringle domains, an event that triggers a structural re-arrangement of plasminogen to an open conformation. Upon converting from closed to open conformation, the activation loop between KR-5 and SP domains becomes exposed, and is cleaved by plasminogen activators (such as tissue plasminogen activator or urokinase plasminogen activator) to form the enzymatically active form, plasmin (Plm). The plasminogen activation system is tightly regulated by host serine protease inhibitors: plasminogen activation inhibitors 1 and 2 (PAI-1 and PAI-2). Active plasmin released from targets is typically removed from circulation by specific inhibitors alpha-2-antiplasmin or the housekeeping enzyme alpha-2-macroglobulin.

The term "plasminogen" as provided herein includes any of the variants of plasminogen, including Glu-plasminogen (Glu-Plg), Lys-plasminogen (Lys-Plg), and mini-, midi- and micro-plasminogens. Lys-plasminogen is an N-truncated form of Glu-Plg that is formed from the cleavage of Glu-plasminogen by plasmin. Lys-plasminogen exhibits higher affinity for fibrin compared to Glu-Plg and is better activated by uPA and tPA. Midi-plasminogen comprises kringle domains 4 and 5 and the light chain (serine protease domain) of plasminogen. It is formed by cleavage of kringle domains 1 to 3 from Glu-plasminogen. Mini-plasminogen (also known as 442Val-Plg or neoplasminogen) results from the action of elastase on Glu-plasminogen at residue 442 (located within Kringle domain 4). Thus mini-plasminogen comprises part of kringle domain 4, kringle domain 5 and the serine protease domain of plasminogen. Micro-plasminogen consists of the proenzyme domain of plasminogen with a stretch of connecting peptide and a few residues of kringle 5 attached at its N-terminal end. It is produced by the action of plasmin on plasminogen. Thus, micro-plasminogen (or micro-Plg) comprises the light chain of plasminogen (serine protease domain) and no kringle domains. (See, for example, Shi et al. (1980) J Biol. Chem. 263:17071-5). Like plasminogen, microplasminogen is activated by tPA and urokinase to form a proteolytically active molecule. Human microplasmin has a molecular weight of approximately 29 kDa and has a lower affinity for fibrin when compared with plasmin.

For the purposes of nomenclature only and not a limitation, an exemplary amino acid sequence of human plasminogen ("glu-PLG) is set forth in SEQ ID NO: 33. The sequence comprising the hPIm serine protease domain is set forth in SEQ ID NO: 34, with the catalytic triad residues underlined and shown in bold.

As used herein, reference to plasmin is to a molecule that has at least one biochemical or biophysical activity of plasmin. The biochemical or biophysical activities, and structure of plasmin can be distinguished from those of plasminogen.

The phrase "inhibits plasmin activity" or "reduces plasmin activity" is understood to mean that the antigen binding protein of the present invention inhibits or reduces the enzyme activity of plasmin. Further, the activity is measured using a suitable in vitro, cellular or in vivo assay and the activity is blocked or reduced by at least 1%, 5%, 10%, 25%, 50%, 60%, 70%, 80% or 90% or more, compared to plasmin activity in the same assay under the same conditions but without the antigen binding protein. Preferably, the plasmin activity is measured after activation of plasminogen by any one or more plasminogen activators. A plasminogen activator is any enzyme that can cleave the $Arg_{561}$-$Val_{562}$ bond (numbering as per human plasminogen). Exemplary plasminogen-cleaving serine proteases, therefore plasminogen activators, include the coagulation proteins factor IX, factor X, and prothrombin (factor II), protein C, chymotrypsin and trypsin, various leukocyte elastases, the streptokinase (SK), urokinase (uPA) and tissue plasminogen activator (tPA), and plasmin.

The term "isolated protein" or "isolated polypeptide" is a protein or polypeptide that by virtue of its origin or source of derivation is not associated with naturally-associated components that accompany it in its native state, is substantially free of other proteins from the same source. A protein may be rendered substantially free of naturally associated components or substantially purified by isolation, using protein purification techniques known in the art. By "substantially purified" is meant the protein is substantially free of contaminating agents, e.g., at least about 70% or 75% or 80% or 85% or 90% or 95% or 96% or 97% or 98% or 99% free of contaminating agents.

The term "recombinant" shall be understood to mean the product of artificial genetic recombination. Accordingly, in the context of a recombinant protein comprising an antibody antigen binding domain, this term does not encompass an antibody naturally-occurring within a subject's body that is the product of natural recombination that occurs during B cell maturation. However, if such an antibody is isolated, it is to be considered an isolated protein comprising an antibody antigen binding domain. Similarly, if nucleic acid encoding the protein is isolated and expressed using recombinant means, the resulting protein is a recombinant protein comprising an antibody antigen binding domain. A recombinant protein also encompasses a protein expressed by artificial recombinant means when it is within a cell, tissue or subject, e.g., in which it is expressed.

The term "protein" shall be taken to include a single polypeptide chain, i.e., a series of contiguous amino acids linked by peptide bonds or a series of polypeptide chains covalently or non-covalently linked to one another (i.e., a polypeptide complex). For example, the series of polypeptide chains can be covalently linked using a suitable chemical or a disulphide bond. Examples of non-covalent bonds include hydrogen bonds, ionic bonds, van der Waals forces, and hydrophobic interactions. The protein may include one or more non-natural amino acids.

The term "polypeptide" or "polypeptide chain" will be understood from the foregoing paragraph to mean a series of contiguous amino acids linked by peptide bonds.

As used herein, the term "antigen binding domain" and shall be taken to mean a region of an antibody that is capable of specifically binding to an antigen, i.e., a VH or a VL or an Fv comprising both a VH and a VL. The antigen binding domain need not be in the context of an entire antibody, e.g., it can be in isolation (e.g., a domain antibody) or in another form, e.g., as described herein, such as a scFv.

For the purposes for the present disclosure, the term "antibody" includes a protein capable of specifically binding to one or a few closely related antigens (e.g., plasmin) by virtue of an antigen binding domain contained within an Fv. This term includes four chain antibodies (e.g., two light chains and two heavy chains), recombinant or modified antibodies (e.g., chimeric antibodies, humanized antibodies, human antibodies, CDR-grafted antibodies, primatized antibodies, de-immunized antibodies, synhumanized antibodies, half-antibodies, bispecific antibodies). The antibody may further comprise a chemical modification, such as conjugation to an active agent or radiolabel, or an agent for improving solubility, for example pegylation of the antibodies described herein or antigen binding fragments thereof.

An antibody generally comprises constant domains, which can be arranged into a constant region or constant fragment or fragment crystallizable (Fc). Exemplary forms of antibodies comprise a four-chain structure as their basic unit. Full-length antibodies comprise two heavy chains (~50 to 70 kD) covalently linked and two light chains (~23 kDa each). A light chain generally comprises a variable region (if present) and a constant domain and in mammals is either a κ light chain or a λ light chain. A heavy chain generally comprises a variable region and one or two constant domain(s) linked by a hinge region to additional constant domain(s). Heavy chains of mammals are of one of the following types α, δ, ε, γ, or μ. Each light chain is also covalently linked to one of the heavy chains. For example, the two heavy chains and the heavy and light chains are held together by inter-chain disulfide bonds and by non-covalent interactions. The number of inter-chain disulfide bonds can vary among different types of antibodies. Each chain has an N-terminal variable region (VH or VL wherein each are ~110 amino acids in length) and one or more constant domains at the C-terminus. The constant domain of the light chain (CL which is ~110 amino acids in length) is aligned with and disulfide bonded to the first constant domain of the heavy chain (CH1 which is 330 to 440 amino acids in length). The light chain variable region is aligned with the variable region of the heavy chain. The antibody heavy chain can comprise 2 or more additional CH domains (such as, CH2, CH3 and the like) and can comprise a hinge region between the CH1 and CH2 constant domains. Antibodies can be of any type (e.g., IgG, IgE, IgM, IgD, IgA, and IgY), class (e.g., IgG1, IgG2, IgG3, IgG4, IgA1 and IgA2) or subclass. In one example, the antibody is a murine (mouse or rat) antibody or a primate (such as, human) antibody. In one example the antibody heavy chain is missing a C-terminal lysine residue. In one example, the antibody is humanized, synhumanized, chimeric, CDR-grafted or deimmunized.

The terms "full-length antibody", "intact antibody" or "whole antibody" are used interchangeably to refer to an antibody in its substantially intact form, as opposed to an antigen binding fragment of an antibody. Specifically, whole antibodies include those with heavy and light chains including an Fc region. The constant domains may be wild-type sequence constant domains (e.g., human wild-type sequence constant domains) or amino acid sequence variants thereof.

As used herein, "variable region" refers to the portions of the light and/or heavy chains of an antibody as defined herein that is capable of specifically binding to an antigen and, includes amino acid sequences of complementarity determining regions (CDRs); i.e., CDR1, CDR2, and CDR3, and framework regions (FRs). For example, the variable region comprises three or four FRs (e.g., FR1, FR2, FR3 and optionally FR4) together with three CDRs. VH refers to the variable region of the heavy chain. VL refers to the variable region of the light chain.

As used herein, the term "complementarity determining regions" (syn. CDRs; i.e., CDR1, CDR2, and CDR3) refers to the amino acid residues of an antibody variable region the presence of which are major contributors to specific antigen binding. Each variable region domain (VH or VL) typically has three CDRs identified as CDR1, CDR2 and CDR3. The CDRs of VH are also referred to herein as CDR H1, CDR H2 and CDR H3, respectively, wherein CDR H1 corresponds to CDR 1 of VH, CDR H2 corresponds to CDR 2 of VH and CDR H3 corresponds to CDR 3 of VH. Likewise, the CDRs of VL are referred to herein as CDR L1, CDR L2 and CDR L3, respectively, wherein CDR L1 corresponds to CDR 1 of VL, CDR L2 corresponds to CDR 2 of VL and CDR L3 corresponds to CDR 3 of VL. In one example, the amino acid positions assigned to CDRs and FRs are defined according to Kabat Sequences of Proteins of Immunological Interest, National Institutes of Health, Bethesda, Md., 1987 and 1991 (also referred to herein as "the Kabat numbering system"). In another example, the amino acid positions assigned to CDRs and FRs are defined according to the Enhanced Chothia Numbering Scheme (http://www.bioinfo.org.uk/mdex.html). The present invention is not limited to FRs and CDRs as defined by the Kabat numbering system, but includes all numbering systems, including the canonical numbering system or of Chothia and Lesk J. Mol. Biol. 196: 901-917, 1987; Chothia et al., Nature 342: 877-883, 1989; and/or AI-Lazikani et al., J. Mol. Biol. 273: 927-948, 1997; the numbering system of Honnegher and Plükthun J. Mol. Biol. 309: 657-670, 2001; or the IMGT system discussed in Giudicelli et al., Nucleic Acids Res. 25: 206-211 1997. In one example, the CDRs are defined according to the Kabat numbering system. Optionally, heavy chain CDR2 according to the Kabat numbering system does not comprise the five C-terminal amino acids listed herein or any one or more of those amino acids are substituted with another naturally-occurring amino acid.

In this regard, Padlan et al., FASEB J., 9: 133-139, 1995 established that the five C-terminal amino acids of heavy chain CDR2 are not generally involved in antigen binding. "Framework regions" (FRs) are those variable region residues other than the CDR residues. The FRs of VH are also referred to herein as FR H1, FR H2, FR H3 and FR H4, respectively, wherein FR H1 corresponds to FR 1 of VH, FR H2 corresponds to FR 2 of VH, FR H3 corresponds to FR 3 of VH and FR H4 corresponds to FR 4 of VH. Likewise, the FRs of VL are referred to herein as FR L1, FR L2, FR L3 and FR L4, respectively, wherein FR L1 corresponds to FR 1 of VL, FR L2 corresponds to FR 2 of VL, FR L3 corresponds to FR 3 of VL and FR L4 corresponds to FR 4 of VL.

As used herein, the term "Fv" shall be taken to mean any protein, whether comprised of multiple polypeptides or a single polypeptide, in which a VL and a VH associate and form a complex having an antigen binding domain, i.e., capable of specifically binding to an antigen. The VH and the VL which form the antigen binding domain can be in a single polypeptide chain or in different polypeptide chains. Furthermore, an Fv of the invention (as well as any protein of the invention) may have multiple antigen binding domains which may or may not bind the same antigen. This term shall be understood to encompass fragments directly derived from an antibody as well as proteins corresponding to such a fragment produced using recombinant means. In some examples, the VH is not linked to a heavy chain constant domain (CH) 1 and/or the VL is not linked to a light chain constant domain (CL). Exemplary Fv containing polypeptides or proteins include a Fab fragment, a Fab' fragment, a F(ab') fragment, a scFv, a diabody, a triabody, a tetrabody or higher order complex, or any of the foregoing linked to a constant region or domain thereof, e.g., CH2 or CH3 domain, e.g., a minibody. A "Fab fragment" consists of a monovalent antigen-binding fragment of an immunoglobulin, and can be produced by digestion of a whole antibody with the enzyme papain, to yield a fragment consisting of an intact light chain and a portion of a heavy chain or can be produced using recombinant means. A "Fab' fragment" of an antibody can be obtained by treating a whole antibody with pepsin, followed by reduction, to yield a molecule consisting of an intact light chain and a portion of a heavy chain comprising a VH and a single constant domain. Two Fab' fragments are obtained per antibody treated in this manner. A Fab' fragment can also be produced by recombinant means. A "F(ab')2 fragment" of an antibody consists of a dimer of two Fab' fragments held together by two disulfide bonds, and is obtained by treating a whole antibody molecule with the enzyme pepsin, without subsequent reduction. A "Fab2" fragment is a recombinant fragment comprising two Fab fragments linked using, for example a leucine zipper or a CH3 domain. A "single chain Fv" or "scFv" is a recombinant molecule containing the variable region fragment (Fv) of an antibody in which the variable region of the light chain and the variable region of the heavy chain are covalently linked by a suitable, flexible polypeptide linker.

As used herein, the term "binds" in reference to the interaction of an antigen binding site or an antigen binding domain thereof with an antigen means that the interaction is dependent upon the presence of a particular structure (e.g., an antigenic determinant or epitope) on the antigen. For example, an antibody recognizes and binds to a specific protein structure rather than to proteins generally. If an antibody binds to epitope "A", the presence of a molecule containing epitope "A" (or free, unlabelled "A"), in a reaction containing labeled "A" and the protein, will reduce the amount of labelled "A" bound to the antibody.

As used herein, the term "specifically binds" or "binds specifically" shall be taken to mean that an antigen binding protein of the invention reacts or associates more frequently, more rapidly, with greater duration and/or with greater affinity with a particular antigen or cell expressing same than it does with alternative antigens or cells. For example, an antigen binding protein binds to plasmin (e.g., human plasmin) with materially greater affinity (e.g., 1.5 fold or 2 fold or 5 fold or 10 fold or 20 fold or 40 fold or 60 fold or 80 fold to 100 fold or 150 fold or 200 fold) than it does to other related molecules, such as other serine proteases. In an example of the present invention, an antigen binding protein that "specifically binds" to plasmin (preferably human) with an affinity at least 1.5 fold or 2 fold or greater (e.g., 5 fold or 10 fold or 20 fold r 50 fold or 100 fold or 200 fold) than it does to related serine proteases. Generally, but not necessarily, reference to binding means specific binding, and each term shall be understood to provide explicit support for the other term.

As used herein, the term "does not detectably bind" shall be understood to mean that an antigen binding protein, e.g. an antibody, binds to a candidate antigen at a level less than 10%, or 8% or 6% or 5% above background. The background can be the level of binding signal detected in the absence of the protein and/or in the presence of a negative control protein (e.g., an isotype control antibody) and/or the level of binding detected in the presence of a negative control antigen. The level of binding is detected using biosensor analysis (e.g. Biacore) in which the antigen binding protein is immobilized and contacted with an antigen.

As used herein, the term "does not significantly bind" shall be understood to mean that the level of binding of an antigen binding protein of the invention to a polypeptide is not statistically significantly higher than background, e.g., the level of binding signal detected in the absence of the antigen binding protein and/or in the presence of a negative control protein (e.g., an isotype control antibody) and/or the level of binding detected in the presence of a negative control polypeptide. The level of binding is detected using biosensor analysis (e.g. Biacore) in which the antigen binding protein is immobilized and contacted with an antigen.

As used herein, the term "epitope" (syn. "antigenic determinant") shall be understood to mean a region of plasmin to which an antigen binding protein comprising an antigen binding domain of an antibody binds. Unless otherwise defined, this term is not necessarily limited to the specific residues or structure to which the antigen binding protein makes contact. For example, this term includes the region spanning amino acids contacted by the antigen binding protein and 5-10 (or more) or 2-5 or 1-3 amino acids outside of this region. In some examples, the epitope comprises a series of discontinuous amino acids that are positioned close to one another when antigen binding protein is folded, i.e., a "conformational epitope". The skilled artisan will also be aware that the term "epitope" is not limited to peptides or polypeptides. For example, the term "epitope" includes chemically active surface groupings of molecules such as sugar side chains, phosphoryl side chains, or sulfonyl side chains, and, in certain examples, may have specific three dimensional structural characteristics, and/or specific charge characteristics.

As used herein, the term "condition" refers to a disruption of or interference with normal function, and is not to be limited to any specific condition, and will include diseases or disorders.

As used herein, the terms "preventing", "prevent" or "prevention" include administering an antigen binding protein of the invention to thereby stop or hinder the development of at least one symptom of a condition. This term also encompasses treatment of a subject in remission to prevent or hinder relapse.

As used herein, the terms "treating", "treat" or "treatment" include administering an antigen binding protein described herein to thereby reduce or eliminate at least one symptom of a specified disease or condition.

As used herein, the term "subject" shall be taken to mean any animal including humans, for example a mammal. Exemplary subjects include but are not limited to humans and non-human primates. For example, the subject is a human.

Antibodies

In one example, an antigen binding protein or plasmin-binding protein as described herein according to any example is an antibody.

Methods for generating antibodies are known in the art and/or described in Harlow and Lane (editors) Antibodies: A Laboratory Manual, Cold Spring Harbor Laboratory, (1988). Generally, in such methods plasmin (e.g., human plasmin) or a region thereof (e.g., an extracellular region) or immunogenic fragment or epitope thereof or a cell expressing and displaying same (i.e., an immunogen), optionally formulated with any suitable or desired carrier, adjuvant, or pharmaceutically acceptable excipient, is administered to a non-human animal, for example, a mouse, chicken, rat, rabbit, guinea pig, dog, horse, cow, goat or pig. The immunogen may be administered intranasally, intramuscularly, subcutaneously, intravenously, intradermally, intraperitoneally, or by other known routes.

The production of polyclonal antibodies may be monitored by sampling blood of the immunized animal at various points following immunization. One or more further immunizations may be given, if required to achieve a desired antibody titer. The process of boosting and titering is repeated until a suitable titer is achieved. When a desired level of immunogenicity is obtained, the immunized animal is bled and the serum isolated and stored, and/or the animal is used to generate monoclonal antibodies (mAbs).

Monoclonal antibodies are one exemplary form of antibody contemplated by the present invention. The term "monoclonal antibody" or "mAb" refers to a homogeneous antibody population capable of binding to the same antigen(s), for example, to the same epitope within the antigen. This term is not intended to be limited with regard to the source of the antibody or the manner in which it is made.

For the production of mAbs any one of a number of known techniques may be used, such as, for example, the procedure exemplified in U.S. Pat. No. 4,196,265 or Harlow and Lane (1988), supra.

For example, a suitable animal is immunized with an immunogen under conditions sufficient to stimulate antibody producing cells. Rodents such as rabbits, mice and rats are exemplary animals. Mice genetically-engineered to express human antibodies, for example, which do not express murine antibodies, can also be used to generate an antibody of the present invention (e.g., as described in WO2002/066630).

Following immunization, somatic cells with the potential for producing antibodies, specifically B lymphocytes (B cells), are selected for use in the mAb generating protocol. These cells may be obtained from biopsies of spleens, tonsils or lymph nodes, or from a peripheral blood sample. The B cells from the immunized animal are then fused with cells of an immortal myeloma cell, generally derived from the same species as the animal that was immunized with the immunogen.

Hybrids are amplified by culture in a selective medium comprising an agent that blocks the de novo synthesis of nucleotides in the tissue culture media. Exemplary agents are aminopterin, methotrexate and azaserine.

The amplified hybridomas are subjected to a functional selection for antibody specificity and/or titer, such as, for example, by flow cytometry and/or immunohistochemstry and/or immunoassay (e.g. radioimmunoassay, enzyme immunoassay, cytotoxicity assay, plaque assay, dot immunoassay, and the like).

Alternatively, ABL-MYC technology (NeoClone, Madison Wis. 53713, USA) is used to produce cell lines secreting MAbs (e.g., as described in Largaespada et al, *J. Immunol. Methods*. 197: 85-95, 1996).

Antibodies can also be produced or isolated by screening a display library, e.g., a phage display library, e.g., as described in U.S. Pat. No. 6,300,064 and/or U.S. Pat. No. 5,885,793. For example, the present inventors have isolated fully human antibodies from a phage display library.

The antibody of the present invention may be a synthetic antibody. For example, the antibody is a chimeric antibody, a humanized antibody, a human antibody synhumanized antibody, primatized antibody or a de-immunized antibody.

Antibody Binding Domain Containing Proteins

Single-Domain Antibodies

In some examples, a protein of the invention is or comprises a single-domain antibody (which is used interchangeably with the term "domain antibody" or "dAb"). A single-domain antibody is a single polypeptide chain comprising all or a portion of the heavy chain variable region of an antibody. In certain examples, a single-domain antibody is a human single-domain antibody (Domantis, Inc., Waltham, Mass.; see, e.g., U.S. Pat. No. 6,248,516).

Diabodies, Triabodies, Tetrabodies

In some examples, a protein of the invention is or comprises a diabody, triabody, tetrabody or higher order protein complex such as those described in WO98/044001 and/or WO94/007921.

For example, a diabody is a protein comprising two associated polypeptide chains, each polypeptide chain comprising the structure $V_L$-X-$V_H$ or $V_H$-X-$V_L$, wherein $V_L$ is an antibody light chain variable region, $V_H$ is an antibody heavy chain variable region, X is a linker comprising insufficient residues to permit the $V_H$ and $V_L$ in a single polypeptide chain to associate (or form an Fv) or is absent, and wherein the $V_H$ of one polypeptide chain binds to a $V_L$ of the other polypeptide chain to form an antigen binding domain, i.e., to form a Fv molecule capable of specifically binding to one or more antigens. The $V_L$ and $V_H$ can be the same in each polypeptide chain or the $V_L$ and $V_H$ can be different in each polypeptide chain so as to form a bispecific diabody (i.e., comprising two Fvs having different specificity).

Single Chain Fv (scFv)

The skilled artisan will be aware that scFvs comprise $V_H$ and $V_L$ regions in a single polypeptide chain and a polypeptide linker between the $V_H$ and $V_L$ which enables the scFv to form the desired structure for antigen binding (i.e., for the $V_H$ and $V_L$ of the single polypeptide chain to associate with one another to form a Fv). For example, the linker comprises in excess of 12 amino acid residues with $(Gly_4Ser)_3$ being one of the more favored linkers for a scFv.

The present invention also contemplates a disulfide stabilized Fv (or diFv or dsFv), in which a single cysteine residue is introduced into a FR of $V_H$ and a FR of $V_L$ and the cysteine residues linked by a disulfide bond to yield a stable Fv.

Alternatively, or in addition, the present invention encompasses a dimeric scFv, i.e., a protein comprising two scFv molecules linked by a non-covalent or covalent linkage, e.g., by a leucine zipper domain (e.g., derived from Fos or Jun). Alternatively, two scFvs are linked by a peptide linker of sufficient length to permit both scFvs to form and to bind to an antigen, e.g., as described in US20060263367.

Heavy Chain Antibodies

Heavy chain antibodies differ structurally from many other forms of antibodies, in so far as they comprise a heavy chain, but do not comprise a light chain. Accordingly, these antibodies are also referred to as "heavy chain only antibodies". Heavy chain antibodies are found in, for example, camelids and cartilaginous fish (also called IgNAR).

The variable regions present in naturally occurring heavy chain antibodies are generally referred to as "$V_{HH}$ domains" in camelid antibodies and V-NAR in IgNAR, in order to distinguish them from the heavy chain variable regions that are present in conventional 4-chain antibodies (which are referred to as "$V_H$ domains") and from the light chain variable regions that are present in conventional 4-chain antibodies (which are referred to as "$V_L$ domains").

A general description of heavy chain antibodies from camelids and the variable regions thereof and methods for their production and/or isolation and/or use is found inter alia in the following references WO94/04678, WO97/49805 and WO 97/49805.

A general description of heavy chain antibodies from cartilaginous fish and the variable regions thereof and methods for their production and/or isolation and/or use is found inter alia in WO2005/118629.

Other Antibodies and Proteins Comprising Antigen Binding Domains Thereof

The present invention also contemplates other antibodies and proteins comprising antigen-binding domains thereof, such as:

(i) "key and hole" bispecific proteins as described in U.S. Pat. No. 5,731,168;

(ii) heteroconjugate proteins, e.g., as described in U.S. Pat. No. 4,676,980;

(iii) heteroconjugate proteins produced using a chemical cross-linker, e.g., as described in U.S. Pat. No. 4,676,980; and (iv) $Fab_3$ (e.g., as described in EP19930302894).

Mutations to Proteins

The present invention also provides an antigen binding protein or a nucleic acid encoding same having at least 80% identity to a sequence disclosed herein. In one example, an antigen binding protein or nucleic acid of the invention comprises sequence at least about 85% or 90% or 95% or 97% or 98% or 99% identical to a sequence disclosed herein.

Alternatively, or additionally, the antigen binding protein comprises a CDR (e.g., three CDRs) at least about 80% or 85% or 90% or 95% or 97% or 98% or 99% identical to CDR(s) of a $V_H$ or $V_L$ as described herein according to any example.

In another example, a nucleic acid of the invention comprises a sequence at least about 80% or 85% or 90% or 95% or 97% or 98% or 99% identical to a sequence encoding an antigen binding protein having a function as described herein according to any example. The present invention also encompasses nucleic acids encoding an antigen binding protein of the invention, which differs from a sequence exemplified herein as a result of degeneracy of the genetic code.

The % identity of a nucleic acid or polypeptide is determined by GAP (Needleman and Wunsch. *Mol. Biol.* 48, 443-453, 1970) analysis (GCG program) with a gap creation penalty=5, and a gap extension penalty=0.3. The query sequence is at least 50 residues in length, and the GAP analysis aligns the two sequences over a region of at least 50 residues. For example, the query sequence is at least 100 residues in length and the GAP analysis aligns the two sequences over a region of at least 100 residues. For example, the two sequences are aligned over their entire length.

The present invention also contemplates a nucleic acid that hybridizes under stringent hybridization conditions to a nucleic acid encoding an antigen binding protein described herein. A "moderate stringency" is defined herein as being a hybridization and/or washing carried out in 2×SSC buffer, 0.1% (w/v) SDS at a temperature in the range 45° C. to 65° C., or equivalent conditions. A "high stringency" is defined herein as being a hybridization and/or wash carried out in 0.1×SSC buffer, 0.1% (w/v) SDS, or lower salt concentration, and at a temperature of at least 65° C., or equivalent conditions. Reference herein to a particular level of stringency encompasses equivalent conditions using wash/hybridization solutions other than SSC known to those skilled in the art. For example, methods for calculating the temperature at which the strands of a double stranded nucleic acid will dissociate (also known as melting temperature, or Tm) are known in the art. A temperature that is similar to (e.g., within 5° C. or within 10° C.) or equal to the Tm of a nucleic acid is considered to be high stringency. Medium stringency is to be considered to be within 10° C. to 20° C. or 10° C. to 15° C. of the calculated Tm of the nucleic acid.

The present invention also contemplates mutant forms of an antigen binding protein of the invention comprising one or more conservative amino acid substitutions compared to a sequence set forth herein. In some examples, the antigen binding protein comprises 10 or fewer, e.g., 9 or 8 or 7 or 6 or 5 or 4 or 3 or 2 or 1 conservative amino acid substitutions. A "conservative amino acid substitution" is one in which the amino acid residue is replaced with an amino acid residue having a similar side chain and/or hydropathicity and/or hydrophilicity.

Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), #-branched side chains (e.g., threonine, valine, isoleucine) and aromatic side chains (e.g., tyrosine, phenylalanine, tryptophan, histidine). Hydropathic indices are described, for example in Kyte and Doolittle *J. Mol. Biol.,* 157: 105-132, 1982 and hydrophylic indices are described in, e.g., U.S. Pat. No. 4,554,101.

The present invention also contemplates non-conservative amino acid changes. For example, of particular interest are substitutions of charged amino acids with another charged amino acid and with neutral or positively charged amino acids. In some examples, the antigen binding protein comprises 10 or fewer, e.g., 9 or 8 or 7 or 6 or 5 or 4 or 3 or 2 or 1 non-conservative amino acid substitutions.

In one example, the mutation(s) occur within a FR of an antigen binding domain of an antigen binding protein of the invention. In another example, the mutation(s) occur within a CDR of an antigen binding protein of the invention.

Exemplary methods for producing mutant forms of an antigen binding protein include:

mutagenesis of DNA (Thie et al., *Methods Mol. Biol.* 525: 309-322, 2009) or RNA (Kopsidas et al., *Immunol. Lett.* 107:163-168, 2006; Kopsidas et al. *BMC Biotechnology,* 7: 18, 2007; and WO1999/058661);

introducing a nucleic acid encoding the polypeptide into a mutator cell, e.g., XL-1 Red, XL-mutS and XL-mutS-Kanr bacterial cells (Stratagene);

DNA shuffling, e.g., as disclosed in Stemmer, *Nature* 370: 389-91, 1994; and site directed mutagenesis, e.g., as described in Dieffenbach (ed) and Dveksler (ed) (In: PCR Primer: A Laboratory Manual, Cold Spring Harbor Laboratories, N Y, 1995).

Exemplary methods for determining biological activity of the mutant antigen binding proteins of the invention will be apparent to the skilled artisan and/or described herein, e.g., antigen binding. For example, methods for determining antigen binding, competitive inhibition of binding, affinity, association, dissociation and therapeutic efficacy are described herein.

Constant Regions

The present invention encompasses antigen binding proteins and/or antibodies described herein comprising a constant region of an antibody. This includes antigen binding fragments of an antibody fused to an Fc.

Sequences of constant regions useful for producing the proteins of the present invention may be obtained from a number of different sources. In some examples, the constant region or portion thereof of the protein is derived from a human antibody. The constant region or portion thereof may be derived from any antibody class, including IgM, IgG, IgD, IgA and IgE, and any antibody isotype, including IgG1, IgG2, IgG3 and IgG4. In one example, the constant region is human isotype IgG4 or a stabilized IgG4 constant region.

In one example, the Fc region of the constant region has a reduced ability to induce effector function, e.g., compared to a native or wild-type human IgG1 or IgG3 Fc region. In one example, the effector function is antibody-dependent cell-mediated cytotoxicity (ADCC) and/or antibody-dependent cell-mediated phagocytosis (ADCP) and/or complement-dependent cytotoxicity (CDC). Methods for assessing the level of effector function of an Fc region containing protein are known in the art and/or described herein.

In one example, the Fc region is an IgG4 Fc region (i.e., from an IgG4 constant region), e.g., a human IgG4 Fc region. Sequences of suitable IgG4 Fc regions will be apparent to the skilled person and/or available in publically available databases (e.g., available from National Center for Biotechnology Information).

In one example, the constant region is a stabilized IgG4 constant region. The term "stabilized IgG4 constant region" will be understood to mean an IgG4 constant region that has been modified to reduce Fab arm exchange or the propensity to undergo Fab arm exchange or formation of a half-antibody or a propensity to form a half antibody. "Fab arm exchange" refers to a type of protein modification for human IgG4, in which an IgG4 heavy chain and attached light chain (half-molecule) is swapped for a heavy-light chain pair from another IgG4 molecule. Thus, IgG4 molecules may acquire two distinct Fab arms recognizing two distinct antigens (resulting in bispecific molecules). Fab arm exchange occurs naturally in vivo and can be induced in vitro by purified blood cells or reducing agents such as reduced glutathione. A "half antibody" forms when an IgG4 antibody dissociates to form two molecules each containing a single heavy chain and a single light chain.

In one example, a stabilized IgG4 constant region comprises a proline at position 241 of the hinge region according to the system of Kabat (Kabat et al., Sequences of Proteins of Immunological Interest Washington D.C. United States Department of Health and Human Services, 1987 and/or 1991). This position corresponds to position 228 of the hinge region according to the EU numbering system (Kabat et al., Sequences of Proteins of Immunological Interest Washington D.C. United States Department of Health and Human Services, 2001 and Edelman et al., Proc. Natl. Acad. USA, 63, 78-85, 1969). In human IgG4, this residue is generally a serine. Following substitution of the serine for proline, the IgG4 hinge region comprises a sequence CPPC. In this regard, the skilled person will be aware that the "hinge region" is a proline-rich portion of an antibody heavy chain constant region that links the Fc and Fab regions that confers mobility on the two Fab arms of an antibody. The hinge region includes cysteine residues which are involved in inter-heavy chain disulfide bonds. It is generally defined as stretching from Glu226 to Pro243 of human IgG1 according to the numbering system of Kabat. Hinge regions of other IgG isotypes may be aligned with the IgG1 sequence by placing the first and last cysteine residues forming inter-heavy chain disulphide (S—S) bonds in the same positions (see for example WO2010/080538).

Additional examples of stabilized IgG4 antibodies are antibodies in which arginine at position 409 in a heavy chain constant region of human IgG4 (according to the EU numbering system) is substituted with lysine, threonine, methionine, or leucine (e.g., as described in WO2006/033386). The Fc region of the constant region may additionally or alternatively comprise a residue selected from the group consisting of: alanine, valine, glycine, isoleucine and leucine at the position corresponding to 405 (according to the EU numbering system). Optionally, the hinge region comprises a proline at position 241 (i.e., a CPPC sequence) (as described above).

In another example, the Fc region is a region modified to have reduced effector function, i.e., a "non-immunostimulatory Fc region". For example, the Fc region is an IgG1 Fc region comprising a substitution at one or more positions selected from the group consisting of 268, 309, 330 and 331. In another example, the Fc region is an IgG1 Fc region comprising one or more of the following changes E233P, L234V, L235A and deletion of G236 and/or one or more of the following changes A327G, A330S and P331S (Armour et al., Eur J Immunol. 29:2613-2624, 1999; Shields et al., J Biol Chem. 276(9):6591-604, 2001). Additional examples of non-immunostimulatory Fc regions are described, for example, in Dall'Acqua et al., J Immunol. 177: 1129-1138 2006; and/or Hezareh J Virol; 75: 12161-12168, 2001).

In another example, the Fc region is a chimeric Fc region, e.g., comprising at least one $C_H2$ domain from an IgG4 antibody and at least one $C_H3$ domain from an IgG1 antibody, wherein the Fc region comprises a substitution at one or more amino acid positions selected from the group consisting of 240, 262, 264, 266, 297, 299, 307, 309, 323, 399, 409 and 427 (EU numbering) (e.g., as described in WO2010/085682). Exemplary substitutions include 240F, 262L, 264T, 266F, 297Q, 299A, 299K, 307P, 309K, 309M, 309P, 323F, 399S, and 427F.

Additional Modifications

The present invention also contemplates additional modifications to an antibody or antigen binding protein comprising an Fc region or constant region.

For example, the antibody comprises one or more amino acid substitutions that increase the half-life of the protein. For example, the antibody comprises a Fc region comprising one or more amino acid substitutions that increase the affinity of the Fc region for the neonatal Fc region (FcRn). For example, the Fc region has increased affinity for FcRn at lower pH, e.g., about pH 6.0, to facilitate Fc/FcRn binding in an endosome. In one example, the Fc region has increased affinity for FcRn at about pH 6 compared to its affinity at about pH 7.4, which facilitates the re-release of Fc into blood following cellular recycling. These amino acid substitutions are useful for extending the half life of a protein, by reducing clearance from the blood.

Exemplary amino acid substitutions include T250Q and/or M428L or T252A, T254S and T266F or M252Y, S254T and T256E or H433K and N434F according to the EU numbering system. Additional or alternative amino acid substitutions are described, for example, in US20070135620 or U.S. Pat. No. 7,083,784.

Protein Production

In one example, an antigen binding protein described herein according to any example is produced by culturing a hybridoma under conditions sufficient to produce the protein, e.g., as described herein and/or as is known in the art.

Recombinant Expression

In another example, an antigen binding protein described herein according to any example is recombinant.

In the case of a recombinant protein, nucleic acid encoding same can be cloned into expression constructs or vectors, which are then transfected into host cells, such as E. coli cells, yeast cells, insect cells, or mammalian cells, such as simian COS cells, Chinese Hamster Ovary (CHO) cells, human embryonic kidney (HEK) cells, or myeloma cells that do not otherwise produce the protein. Exemplary cells used for expressing a protein are CHO cells, myeloma cells or HEK cells. Molecular cloning techniques to achieve these ends are known in the art and described, for example in Ausubel et al., (editors), Current Protocols in Molecular Biology, Greene Pub. Associates and Wiley-Interscience (1988, including all updates until present) or Sambrook et al., Molecular Cloning: A Laboratory Manual, Cold Spring Harbor Laboratory Press (1989). A wide variety of cloning and in vitro amplification methods are suitable for the construction of recombinant nucleic acids. Methods of producing recombinant antibodies are also known in the art, see, e.g., U.S. Pat. No. 4,816,567 or U.S. Pat. No. 5,530,101.

Following isolation, the nucleic acid is inserted operably linked to a promoter in an expression construct or expression vector for further cloning (amplification of the DNA) or for expression in a cell-free system or in cells.

As used herein, the term "promoter" is to be taken in its broadest context and includes the transcriptional regulatory sequences of a genomic gene, including the TATA box or initiator element, which is required for accurate transcription initiation, with or without additional regulatory elements (e.g., upstream activating sequences, transcription factor binding sites, enhancers and silencers) that alter expression of a nucleic acid, e.g., in response to a developmental and/or external stimulus, or in a tissue specific manner. In the present context, the term "promoter" is also used to describe a recombinant, synthetic or fusion nucleic acid, or derivative which confers, activates or enhances the expression of a nucleic acid to which it is operably linked. Exemplary promoters can contain additional copies of one or more specific regulatory elements to further enhance expression and/or alter the spatial expression and/or temporal expression of said nucleic acid.

As used herein, the term "operably linked to" means positioning a promoter relative to a nucleic acid such that expression of the nucleic acid is controlled by the promoter.

Many vectors for expression in cells are available. The vector components generally include, but are not limited to, one or more of the following: a signal sequence, a sequence encoding a protein (e.g., derived from the information provided herein), an enhancer element, a promoter, and a transcription termination sequence. The skilled artisan will be aware of suitable sequences for expression of a protein. Exemplary signal sequences include prokaryotic secretion signals (e.g., pelB, alkaline phosphatase, penicillinase, Ipp, or heat-stable enterotoxin II), yeast secretion signals (e.g., invertase leader, a factor leader, or acid phosphatase leader) or mammalian secretion signals (e.g., herpes simplex gD signal).

Exemplary promoters active in mammalian cells include cytomegalovirus immediate early promoter (CMV-IE), human elongation factor 1-a promoter (EF1), small nuclear RNA promoters (U1 a and U1 b), a-myosin heavy chain promoter, Simian virus 40 promoter (SV40), Rous sarcoma virus promoter (RSV), Adenovirus major late promoter, β-actin promoter; hybrid regulatory element comprising a CMV enhancer/β-actin promoter or an immunoglobulin promoter or active fragment thereof. Examples of useful mammalian host cell lines are monkey kidney CV1 line transformed by SV40 (COS-7, ATCC CRL 1651); human embryonic kidney line (293 or 293 cells subcloned for growth in suspension culture; baby hamster kidney cells (BHK, ATCC CCL 10); or Chinese hamster ovary cells (CHO).

Typical promoters suitable for expression in yeast cells such as for example a yeast cell selected from the group comprising Pichia pastoris, Saccharomyces cerevisiae and S. pombe, include, but are not limited to, the ADH1 promoter, the GAL1 promoter, the GAL4 promoter, the CUP1 promoter, the PHO5 promoter, the not promoter, the RPR1 promoter, or the TEF1 promoter.

Means for introducing the isolated nucleic acid or expression construct comprising same into a cell for expression are known to those skilled in the art. The technique used for a given cell depends on the known successful techniques. Means for introducing recombinant DNA into cells include microinjection, transfection mediated by DEAE-dextran, transfection mediated by liposomes such as by using lipofectamine (Gibco, MD, USA) and/or cellfectin (Gibco, MD, USA), PEG-mediated DNA uptake, electroporation and microparticle bombardment such as by using DNA-coated tungsten or gold particles (Agracetus Inc., WI, USA) amongst others.

The host cells used to produce the protein may be cultured in a variety of media, depending on the cell type used. Commercially available media such as Ham's FI0 (Sigma), Minimal Essential Medium ((MEM), (Sigma), RPMI-1640 (Sigma), and Dulbecco's Modified Eagle's Medium ((DMEM), Sigma) are suitable for culturing mammalian cells. Media for culturing other cell types discussed herein are known in the art.

Isolation of Proteins

Methods for isolating a protein are known in the art and/or described herein.

Where an antigen binding protein is secreted into culture medium, supernatants from such expression systems can be first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants. Alternatively, or additionally, supernatants can be filtered and/or separated from cells expressing the protein, e.g., using continuous centrifugation.

The antigen binding protein prepared from the cells can be purified using, for example, ion exchange, hydroxyapatite chromatography, hydrophobic interaction chromatography, gel electrophoresis, dialysis, affinity chromatography (e.g., protein A affinity chromatography or protein G chromatography), or any combination of the foregoing. These methods are known in the art and described, for example in WO99/57134 or Ed Harlow and David Lane (editors) Antibodies: A Laboratory Manual, Cold Spring Harbor Laboratory, (1988).

The skilled artisan will also be aware that a protein can be modified to include a tag to facilitate purification or detection, e.g., a poly-histidine tag, e.g., a hexa-histidine tag, or a influenza virus hemagglutinin (HA) tag, or a Simian Virus 5 (V5) tag, or a FLAG tag, or a glutathione S-transferase (GST) tag. The resulting protein is then purified using methods known in the art, such as, affinity purification. For example, a protein comprising a hexa-his tag is purified by contacting a sample comprising the protein with nickel-nitrilotriacetic acid (Ni-NTA) that specifically binds a hexa-his tag immobilized on a solid or semi-solid support, washing the sample to remove unbound protein, and subsequently eluting the bound protein. Alternatively, or in addition a ligand or antibody that binds to a tag is used in an affinity purification method.

Assaying Activity of an Antigen Binding Protein

Binding to Plasmin and Mutants Thereof

It will be apparent to the skilled artisan from the disclosure herein that antigen binding protein of the present invention bind to plasmin. Methods for assessing binding to a protein are known in the art, e.g., as described in Scopes (In: Protein purification: principles and practice, Third Edition, Springer Verlag, 1994). Such a method generally involves immobilizing the antigen binding site and contacting it with labeled antigen (plasmin). Following washing to remove non-specific bound protein, the amount of label and, as a consequence, bound antigen is detected. Of course, the antigen binding protein can be labeled and the antigen immobilized. Panning-type assays can also be used. Alternatively, or additionally, surface plasmon resonance assays can be used.

Optionally, the dissociation constant (Kd), association constant (Ka) and/or affinity constant (Ko) of an immobilized antigen binding protein for plasmin or an epitope thereof is determined. The "Kd" or "Ka" or "Ko" for an plasmin-binding protein is in one example measured by a radiolabeled or fluorescently-labeled plasmin ligand binding assay. In the case of a "Kd", this assay equilibrates the antigen binding protein with a minimal concentration of labeled plasmin or epitope thereof in the presence of a titration series of unlabeled plasmin. Following washing to remove unbound plasmin or epitope thereof, the amount of label is determined, which is indicative of the Kd of the protein.

According to another example the Kd, Ka or Ko is measured by using surface plasmon resonance assays, e.g., using BIAcore surface plasmon resonance (BIAcore, Inc., Piscataway, N.J.) with immobilized plasmin or a region thereof or immobilized antigen binding protein.
Determining inhibitory activity The antigen binding proteins of the invention are preferably capable of inhibiting plasmin activity. Advantageously, the antigen binding proteins of the present invention inhibit plasmin-mediated clot lysis at comparable or significantly greater levels than physiological inhibitors of plasmin activity or pharmacological inhibitors of plasmin activity.

Various assays are known in the art for assessing the ability of a protein to inhibit or reduce plasmin activity.

In one example, the antigen binding protein inhibits proteolysis of any substrate by plasmin. Preferably, the antigen binding protein of the invention binds to plasmin and prevents binding and/or cleavage of a plasmin substrate by the serine protease domain. Preferably, the antigen binding protein of the invention binds to or sterically shields the catalytic triad of plasmin, such that the catalytic triad is unable to cleave a plasmin substrate, wherein the catalytic triad comprises the residues His603, Asp646 and Ala/Ser741 of SEQ ID NO: 33 (which is equivalent to His57, Asp102 and Ser195 using chymotrypsin numbering). Thus, in preferred embodiments, the antigen binding protein of the invention is an anti-catalytic antigen binding protein.

Preferably, the antigen binding protein of the invention inhibits or prevents cleavage of any known substrate of plasmin including but not limited to: fibrin, fibrinogen, Factors V, VIII and X, protease-activated receptor I, fibronectin, thrombospondin, laminin, von Willebrand factor, vitronectin, pro-brain-derived neurotrophic factor, complement C3 and C5, tenascin, osteocalin, CUB domain-containing protein 1 and other proteases such as collagenase.

The antigen binding protein of the invention may also inhibit the binding of streptokinase to plasmin, or inhibit the binding of a pathogen-derived protein which binds to plasmin in a similar mechanism to streptokinase. More specifically, streptokinase secreted by Streptococcus pyogenes is known to wrap around the serine protease domain of plasminogen/plasmin and once bound, activate plasminogen to form plasmin. The antigen binding proteins of the present invention advantageously inhibit the binding of streptokinase to the serine protease domain of plasmin and thereby inhibit plasmin activity mediated through plasminogen activation by streptokinase.

Exemplary methods for determining the inhibition of plasmin activity are described herein, for example at Examples 2, 5 and 6.

The antigen binding proteins of the invention also have utility in applications requiring detection of plasmin and/or plasminogen in a biological sample. For example, the antigen binding proteins of the invention may be useful for diagnostic applications including where the proteins are used in histology and ELISA and similar applications whereby binding of the antigen binding proteins to a target protein can provide useful diagnostic information.
Conditions to be Treated The antigen binding proteins of the invention have utility in minimising or reducing haemorrhage, or bleeding, following surgery, injury or in individuals with coagulation factor deficiency. The use of the antigen binding proteins in this context inhibit plasmin-mediated fibrinolysis or clot dissolution, thereby reducing blood loss and reducing or minimising the requirement for blood transfusion. Blood transfusion is associated with a high risk of mismatch, allergic reactions, multi-organ dysfunction and infection, resulting in an increase in morbitity and mortality.

The antigen binding proteins of the invention may also be used to prevent bleeding in other conditions such as haemophilia, menorrhagia, von Willebrand syndrome and thrombolytic-induced bleeding.

The antigen binding proteins of the invention have utility in the inhibition of fibrinolysis in a number of clinical situations including to reduce bleeding in patients who have undergone cardiac surgery, orthopaedic surgery, neurosurgery, liver transplantation, vascular surgery, thoracic surgery, gynecological surgery, or who have end-stage renal disease, peripartum bleeding, gastrointestinal bleeding, trauma, traumatic brain injury, intracerebral bleeding and subarachnoid haemorrhage. In other words, the antigen binding proteins of the invention have utility in inhibiting plasmin in individuals that are in a hyperfibrinolytic state.

Accordingly, the antigen binding proteins of the invention have utility in inhibiting fibrinolysis in a broad range of scenarios where inhibition of plasmin activity is required.

The antigen binding sites of the present invention are also useful in the treatment or prevention of any condition associated, or caused by, the presence of or increased levels of bacteria which mediate their pathogenesis by streptokinase and related enzymes.

Streptococcus pyogenes, or Group A streptococcus (GAS), is a facultative, Gram-positive coccus which grows in chains and causes numerous infections in humans including pharyngitis, tonsillitis, scarlet fever, cellulitis, erysipelas, rheumatic fever, post-streptococcal glomerulonephritis, necrotizing fasciitis, myonecrosis and lymphangitis.

Thus, the antigen binding proteins of the invention are useful for inhibiting or preventing skin hyperpigmentation or inflammation, impetigo, pharyngitis, tonsillitis, scarlet fever, cellulitis, erysipelas, rheumatic fever, post-streptococcal glomerulonephritis, necrotizing fasciitis, myonecrosis and lymphangitis caused by Streptococcus pyogenes, Streptococcus dysgalactiae or Streptococcus pneumonia.

The antigen binding proteins of the invention are also useful for inhibiting metastasis of tumours, which are also known to recruit the plasmin system. Exemplary cancers treatable with the antigen binding proteins of the invention include cystic and solid tumours, bone and soft tissue tumours, including tumours in anal tissue, bile duct, bladder, blood cells, bowel, brain, breast, carcinoid, cervix, eye, esophagus, head and neck, kidney, larynx, leukemia, liver, lung, lymph nodes, lymphoma, melanoma, mesothelioma, myeloma, ovary, pancreas, penis, prostate, skin (e.g. squamous cell carcinoma), sarcomas, stomach, testes, thyroid, vagina, vulva. Soft tissue tumours include Benign schwannoma Monosomy, Desmoid tumour, lipo-blastoma, lipoma, uterine leiomyoma, clear cell sarcoma, dermatofibrosarcoma, Ewing sarcoma, extraskeletal myxoid chondrosarcoma, liposarcooma myxoid, Alveolar rhabdomyosarcoma and synovial sarcoma. Specific bone tumours include non-ossifying fibroma, unicameral bone cyst, enchon-droma, aneurismal bone cyst, osteoblastoma, chondroblastoma, chondromyxofibroma, ossifying fibroma and adaman-tinoma, Giant cell tumour, fibrous dysplasia, Ewing's sarcoma eosinophilic granuloma, osteosarcoma, chondroma, chondrosarcoma, malignant fibrous histiocytoma and meta-static carcinoma. Leukemias include acute lymphoblastic, acute myeloblastic, chronic lymphocytic and chronic myeloid.

Other examples include breast tumours, colorectal tumu-ors, adenocarcinomas, mesothelioma, bladder tumours, prostate tumours, germ cell tumour, hepatoma/cholongio, carcinoma, neuroendocrine tumours, pituitary neoplasm, small round cell tumour, squamous cell cancer, mela-noma, atypical fibroxanthoma, seminomas, nonseminomas, stromal leydig cell tumours, Sertoli cell tumours, skin tumours, kidney tumours, testicular tumours, brain tumours, ovarian tumours, stomach tumours, oral tumours, bladder tumours, bone tumours, cervical tumours, esophageal tumours, laryngeal tumours, liver tumours, lung tumours, vaginal tumours and Wilm's tumour.

Compositions

In some examples, an antigen binding protein as described herein can be administered orally, parenterally, by inhalation spray, adsorption, absorption, topically (including as a spray or lotion), rectally, nasally, bucally, vaginally, intraventricularly, via an implanted reservoir in dosage for-mulations containing conventional non-toxic pharmaceuti-cally-acceptable carriers, or by any other convenient dosage form. The term "parenteral" as used herein includes subcu-taneous, intravenous, intramuscular, intraperitoneal, intrath-ecal, intraventricular, intrasternal, and intracranial injection or infusion techniques.

Methods for preparing an antigen binding protein into a suitable form for administration to a subject (e.g. a pharma-ceutical composition) are known in the art and include, for example, methods as described in Remington's Pharmaceu-tical Sciences (18th ed., Mack Publishing Co., Easton, Pa., 1990) and U.S. Pharmacopeia: National Formulary (Mack Publishing Company, Easton, Pa., 1984).

The pharmaceutical compositions of this invention are particularly useful for parenteral administration, such as intravenous administration or administration into a body cavity or lumen of an organ or joint. The compositions for administration will commonly comprise a solution of an antigen binding protein dissolved in a pharmaceutically acceptable carrier, for example an aqueous carrier. A variety of aqueous carriers can be used, e.g., buffered saline and the like. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, cal-cium chloride, sodium lactate and the like. The concentra-tion of an antigen binding protein of the present invention in these formulations can vary widely, and will be selected primarily based on fluid volumes, viscosities, body weight and the like in accordance with the particular mode of administration selected and the patient's needs. Exemplary carriers include water, saline, Ringer's solution, dextrose solution, and 5% human serum albumin. Nonaqueous vehicles such as mixed oils and ethyl oleate may also be used. Liposomes may also be used as carriers. The vehicles may contain minor amounts of additives that enhance iso-tonicity and chemical stability, e.g., buffers and preserva-tives.

The antigen binding proteins of the present invention may be formulated for local or topical administration, such as for topical application to the skin or tissue requiring treatment. Formulations for topical administration typically comprise a topical vehicle combined with active agent(s), with or with-out additional optional components. The pharmaceutical compositions of the invention may be in the form of a spray, cream, gel, lotion or the like for topical administration.

Suitable topical vehicles and additional components are well known in the art, and it will be apparent that the choice of a vehicle will depend on the particular physical form and mode of delivery. Topical vehicles include organic solvents such as alcohols (for example, ethanol, iso-propyl alcohol or glycerine), glycols such as butylene, isoprene or propylene glycol, aliphatic alcohols such as lanolin, mixtures of water and organic solvents and mixtures of organic solvents such as alcohol and glycerine, lipid-based materials such as fatty acids, acylglycerols including oils such as mineral oil, and fats of natural or synthetic origin, phosphoglycerides, sphin-golipids and waxes, protein-based materials such as collagen and gelatine, silicone-based materials (both nonvolatile and volatile), and hydrocarbon-based materials such as micro-sponges and polymer matrices.

A composition may further include one or more compo-nents adapted to improve the stability or effectiveness of the applied formulation, such as stabilizing agents, suspending agents, emulsifying agents, viscosity adjusters, gelling agents, preservatives, antioxidants, skin penetration enhanc-ers, moisturizers and sustained release materials. Examples of such components are described in Martindale—The Extra Pharmacopoeia (Pharmaceutical Press, London 1993) and Martin (ed.), Remington's Pharmaceutical Sciences. Formu-lations may comprise microcapsules, such as hydroxymeth-ylcellulose or gelatine-microcapsules, liposomes, albumin microspheres, microemulsions, nanoparticles or nanocap-sules.

A topical formulation may be prepared in a variety of physical forms including, for example, solids, pastes, creams, foams, lotions, gels, powders, aqueous liquids, emulsions, sprays and skin patches. The physical appearance and viscosity of such forms can be governed by the presence and amount of emulsifier(s) and viscosity adjuster(s) present in the formulation. Solids are generally firm and non-pourable and commonly are formulated as bars or sticks, or in particulate form. Solids can be opaque or transparent, and optionally can contain solvents, emulsifiers, moisturizers, emollients, fragrances, dyes/colorants, preservatives and other active ingredients that increase or enhance the efficacy of the final product. Creams and lotions are often similar to one another, differing mainly in their viscosity. Both lotions and creams may be opaque, translucent or clear and often contain emulsifiers, solvents, and viscosity adjusting agents, as well as moisturizers, emollients, fragrances, dyes/colo-rants, preservatives and other active ingredients that increase or enhance the efficacy of the final product. Gels can be prepared with a range of viscosities, from thick or high viscosity to thin or low viscosity. These formulations, like those of lotions and creams, may also contain solvents, emulsifiers, moisturizers, emollients, fragrances, dyes/colorants, preservatives and other active ingredients that increase or enhance the efficacy of the final product. Liquids are thinner than creams, lotions, or gels, and often do not contain emulsifiers. Liquid topical products often contain solvents, emulsifiers, moisturizers, emollients, fragrances, dyes/colorants, preservatives and other active ingredients that increase or enhance the efficacy of the final product.

Emulsifiers for use in topical formulations include, but are not limited to, ionic emulsifiers, cetearyl alcohol, non-ionic emulsifiers like polyoxyethylene oleyl ether, PEG-40 stearate, ceteareth-12, ceteareth-20, ceteareth-30, ceteareth alcohol, PEG-100 stearate and glyceryl stearate. Suitable viscosity adjusting agents include, but are not limited to, protective colloids or nonionic gums such as hydroxyethylcellulose, xanthan gum, magnesium aluminium silicate, silica, microcrystalline wax, beeswax, paraffin, and cetyl palmitate. A gel composition may be formed by the addition of a gelling agent such as chitosan, methyl cellulose, ethyl cellulose, polyvinyl alcohol, polyquaterniums, hydroxyethylceilulose, hydroxypropylcellulose, hydroxypropylmethylcellulose, carbomer or ammoniated glycyrrhizinate. Suitable surfactants include, but are not limited to, nonionic, amphoteric, ionic and anionic surfactants. For example, one or more of dimethicone copolyol, polysorbate 20, polysorbate 40, polysorbate 60, polysorbate 80, lauramide DEA, cocamide DEA, and cocamide MEA, oleyl betaine, cocamidopropyl phosphatidyl PG-dimonium chloride, and ammonium laureth sulfate may be used within topical formulations.

Preservatives include, but are not limited to, antimicrobials such as methylparaben, propylparaben, sorbic acid, benzoic acid, and formaldehyde, as well as physical stabilizers and antioxidants such as vitamin E, sodium ascorbate/ascorbic acid and propyl gallate. Suitable moisturizers include, but are not limited to, lactic acid and other hydroxy acids and their salts, glycerine, propylene glycol, and butylene glycol. Suitable emollients include lanolin alcohol, lanolin, lanolin derivatives, cholesterol, petrolatum, isostearyl neopentanoate and mineral oils. Suitable fragrances and colours include, but are not limited to, FD&C Red No. 40 and FD&C Yellow No. 5. Other suitable additional ingredients that may be included in a topical formulation include, but are not limited to, abrasives, absorbents, anticaking agents, antifoaming agents, antistatic agents, astringents (such as witch hazel), alcohol and herbal extracts such as chamomile extract, binders/excipients, buffering agents, chelating agents, film forming agents, conditioning agents, propellants, opacifying agents, pH adjusters and protectants.

Typical modes of delivery for topical compositions include application using the fingers, application using a physical applicator such as a cloth, tissue, swab, stick or brush, spraying including mist, aerosol or foam spraying, dropper application, sprinkling, soaking, and rinsing. Controlled release vehicles can also be used, and compositions may be formulated for transdermal administration (for example, as a transdermal patch).

Upon formulation, an antigen binding protein of the present invention will be administered in a manner compatible with the dosage formulation and in such amount as is therapeutically/prophylactically effective. Formulations are easily administered in a variety of dosage forms, such as the type of injectable solutions described above, but other pharmaceutically acceptable forms are also contemplated, e.g., tablets, pills, capsules or other solids for oral administration, suppositories, pessaries, nasal solutions or sprays, aerosols, inhalants, liposomal forms, gels, creams, sprays and the like. Pharmaceutical "slow release" capsules or compositions may also be used. Slow release formulations are generally designed to give a constant drug level over an extended period and may be used to deliver an antigen binding protein of the present invention.

WO2002/080967 describes compositions and methods for administering aerosolized compositions comprising antibodies for the treatment of, e.g., asthma, which are also suitable for administration of an antigen binding protein of the present invention.

Dosages and Timing of Administration

Suitable dosages of an antigen binding protein of the present invention will vary depending on the specific an antigen binding protein, the condition to be treated and/or the subject being treated. It is within the ability of a skilled physician to determine a suitable dosage, e.g., by commencing with a sub-optimal dosage and incrementally modifying the dosage to determine an optimal or useful dosage. Alternatively, to determine an appropriate dosage for treatment/prophylaxis, data from the cell culture assays or animal studies are used, wherein a suitable dose is within a range of circulating concentrations that include the $ED_{50}$ of the active compound with little or no toxicity. The dosage may vary within this range depending upon the dosage form employed and the route of administration utilized. A therapeutically/prophylactically effective dose can be estimated initially from cell culture assays. A dose may be formulated in animal models to achieve a circulating plasma concentration range that includes the $IC_{50}$ (i.e., the concentration or amount of the compound which achieves a half-maximal inhibition of symptoms) as determined in cell culture. Such information can be used to more accurately determine useful doses in humans. Levels in plasma maybe measured, for example, by high performance liquid chromatography.

In some examples, a method of the present invention comprises administering a prophylactically or therapeutically effective amount of a protein described herein.

Timing of administration may be determined based on the clinical state of the subject receiving the antigen binding protein of the invention. For example, in circumstances where the subject has suffered a trauma, it will be understood that the antigen binding proteins of the invention find utility in being administered as soon as possible following trauma so as to dampen the state of hyperfibrinolysis of the subject.

The term "therapeutically effective amount" is the quantity which, when administered to a subject in need of treatment, improves the prognosis and/or state of the subject and/or that reduces or inhibits one or more symptoms of a clinical condition described herein to a level that is below that observed and accepted as clinically diagnostic or clinically characteristic of that condition. The amount to be administered to a subject will depend on the particular characteristics of the condition to be treated, the type and stage of condition being treated, the mode of administration, and the characteristics of the subject, such as general health, other diseases, age, sex, genotype, and body weight. A person skilled in the art will be able to determine appropriate dosages depending on these and other factors. Accordingly, this term is not to be construed to limit the present invention to a specific quantity, e.g., weight or amount of protein(s), rather the present invention encompasses any amount of the antigen binding protein(s) sufficient to achieve the stated result in a subject.

As used herein, the term "prophylactically effective amount" shall be taken to mean a sufficient quantity of a protein to prevent or inhibit or delay the onset of one or more detectable symptoms of a clinical condition. The skilled artisan will be aware that such an amount will vary depending on, for example, the specific antigen binding protein (s) administered and/or the particular subject and/or the type or severity or level of condition and/or predisposition (genetic or otherwise) to the condition. Accordingly, this term is not to be construed to limit the present invention to a specific quantity, e.g., weight or amount of antigen binding protein(s), rather the present invention encompasses any amount of the antigen binding protein(s) sufficient to achieve the stated result in a subject.

Kits

The present invention additionally comprises a kit comprising one or more of the following:

(i) an antigen binding protein of the invention or expression construct(s) encoding same;

(ii) a cell of the invention;

(iii) a complex of the invention; or (iii) a pharmaceutical composition of the invention.

In the case of a kit for detecting plasmin, the kit can additionally comprise a detection means, e.g., linked to an antigen binding protein of the invention.

In the case of a kit for therapeutic/prophylactic use, the kit can additionally comprise a pharmaceutically acceptable carrier.

Optionally a kit of the invention is packaged with instructions for use in a method described herein according to any example.

It will be understood that the invention disclosed and defined in this specification extends to all alternative combinations of two or more of the individual features mentioned or evident from the text or drawings. All of these different combinations constitute various alternative aspects of the invention.

TABLE 1

| | | | Summary of amino acid and nucleotide sequences |
|---|---|---|---|
| Antibody ID | Region | SEQ ID NO: | Amino acid or nucleotide sequence |
| B10 | LCDR1 (protein) | 1 | DSGS |
| | LCDR2 (protein) | 2 | GSD |
| | LCDR3 (protein) | 3 | GTADSSTTA |
| | HCDR1 (protein) | 4 | GFIFSDYG |
| | HCDR2 (protein) | 5 | IDDDGGGT |
| | HCDR3 (protein) | 6 | AKAVGYGCTYLGYSCAGSIDA |
| | VL (protein) | 7 | QAALTQPSSVSANPGETVKITCSGGDSGSYGWYQQK APGSAPVTVIYGSDKRPSDIPSRFSGSTSGSTNTLT ITGVQVEDEAIYYCGTADSSTTAAGTTLTVL |
| | VH (protein) | 8 | AVTLDESGGGLQTPGGALSLVCKGSGFIFSDYGMFW VRQAPGKGLEWVAGIDDDGGGTSYYAPAVKGRATIS RDNGQSTVRLQLNNLRAEDTGTYYCAKAVGYGCTYL GYSCAGSIDAWGHGTEVIVSS |
| | LCDR1 (DNA) | 9 | GATAGCGGCTCC |
| | LCDR2 (DNA) | 10 | GGCTCTGAT |
| | LCDR3 (DNA) | 11 | GGCACCGCCGACTCTAGCACCACAGCCG |
| | HCDR1 (DNA) | 12 | GGCTTCATCTTTTCTGACTACGGA |
| | HCDR2 (DNA) | 13 | ATCGACGATGACGGAGGAGGCACCTCC |
| | HCDR3 (DNA) | 14 | GCCAAGGCCGTGGGCTATGGCTGCACATACCTGGGC TATTCTTGTGCAGGCAGCATCGACGCA |
| | VL (DNA) | 15 | CAGGCCGCACTGACCCAGCCTAGCTCCGTGAGCGCC AACCCAGGCGAGACAGTGAAGATCACATGCTCCGGA GGCGATAGCGGCTCCTACGGCTGGTATCAGCAGAAG GCCCCCGGCTCCGCCCCTGTGACCGTGATCTACGGC TCTGATAAGCGGCCAAGCGACATCCCCTCCCGCTTC TCTGGCAGCACATCCGGCTCTACCAATACACTGACC |

TABLE 1-continued

| Summary of amino acid and nucleotide sequences | | | |
|---|---|---|---|
| Antibody ID | Region | SEQ ID NO: | Amino acid or nucleotide sequence |
| | | | ATCACAGGCGTGCAGGTGGAGGATGAGGCCATCTAC TATTGCGGCACCGCCGACTCTAGCACCACAGCCGCC GGCACCACACTGACAGTGCTG |
| | VH (DNA) | 16 | GCCGTGACCCTGGATGAGAGCGGAGGAGGCCTCCAG ACACCCGGCGGCGCCCTGAGCCTGGTGTGCAAGGGC TCCGGCTTCATCTTTTCTGACTACGGAATGTTTTGG GTGCGCCAGGCCCCCGGCAAGGGCCTGGAGTGGGTG GCAGGAATCGACGATGACGGAGGAGGCACCTCCTAC TATGCACCTGCCGTGAAGGGAAGGGCAACCATCAGC AGAGATAACGGCCAGAGCACCGTGAGGCTCCAGCTG AACAATCTGAGAGCCGAGGACACCGGCACATACTAT TGTGCCAAGGCCGTGGGCTATGGCTGCACATACCTG GGCTATTCTTGTGCAGGCAGCATCGACGCATGGGGC CACGGCACCGAAGTGATCGTGAGCAGC |
| | LFR1 (protein) | 17 | QAALTQPSSVSANPGETVKITCSGG |
| | LFR2 (protein) | 18 | YGWYQQKAPGSAPVTVIY |
| | LFR3 (protein) | 19 | KRPSDIPSRFSGSTSGSTNTLTITGVQVEDEAIYYC |
| | LFR4 (protein) | 20 | AGTTLTVL |
| | HFR1 (protein) | 21 | AVTLDESGGGLQTPGGALSLVCKGS |
| | HFR2 (protein) | 22 | MFWVRQAPGKGLEWVAG |
| | HFR3 (protein) | 23 | SYYAPAVKGRATISRDNGQSTVRLQLNNLRAEDTGT YYC |
| | HFR4 (protein) | 24 | WGHGTEVIVSS |
| | LFR1 (DNA) | 25 | CAGGCCGCACTGACCCAGCCTAGCTCCGTGAGCGCC AACCCAGGCGAGACAGTGAAGATCACATGCTCCGGA GGC |
| | LFR2 (DNA) | 26 | TACGGCTGGTATCAGCAGAAGGCCCCCGGCTCCGCC CCTGTGACCGTGATCTAC |
| | LFR3 (DNA) | 27 | AAGCGGCCAAGCGACATCCCCTCCCGCTTCTCTGGC AGCACATCCGGCTCTACCAATACACTGACCATCACA GGCGTGCAGGTGGAGGATGAGGCCATCTACTATTGC |
| | LFR4 (DNA) | 28 | GCCGGCACCACACTGACAGTGCTG |
| | HFR1 (DNA) | 29 | GCCGTGACCCTGGATGAGAGCGGAGGAGGCCTCCAG ACACCCGGCGGCGCCCTGAGCCTGGTGTGCAAGGGC TCC |
| | HFR2 (DNA) | 30 | ATGTTTTGGGTGCGCCAGGCCCCCGGCAAGGGCCTG GAGTGGGTGGCAGGA |
| | HFR3 (DNA) | 31 | TCCTACTATGCACCTGCCGTGAAGGGAAGGGCAACC ATCAGCAGAGATAACGGCCAGAGCACCGTGAGGCTC CAGCTGAACAATCTGAGAGCCGAGGACACCGGCACA TACTATTGT |
| | HFR4 (DNA) | 32 | TGGGGCCACGGCACCGAAGTGATCGTGAGCAGC |
| hPlg (mature sequence shown with signal | — | 33 | EPLDDYVNTQGASLFSVTKKQLGAGSIEECAAKCEE DEEFTCRAFQYHSKEQQCVIMAENRKSSIIIRMRDW LFEKKVYLSECKTGNGKNYRGTMSKTKNGITCQKWS STSPHRPRFSPATHPSEGLEENYCRNPDNDPQGPWC YTTDPEKRYDYCDILECEEECMHCSGENYDGKISKT MSGLECQAWDSQSPHAGYIPSKFPNKNLKKNYCRN |

TABLE 1-continued

Summary of amino acid and nucleotide sequences

| Antibody ID | Region | SEQ ID NO: | Amino acid or nucleotide sequence |
|---|---|---|---|
| peptide removed) | | | PDRELRPWCFTTDPNKRWELCDIPRCTTPPPSSGPT YQCLKGTGENYRGNVAVTVSGHTCQHWSAQTPHTHN RTPENFPCKNLDENYCRNPDGKRAPWCHTTNSQVRW EYCKIPSCDSSPVSTEQLAPTAPPELTPWQDCYHGD GQSYRGTSSTTTTGKKCQSWSSMTPHRHQKTPENYP NAGLTMNYCRNPDADKGPWCFTTDPSVRWEYCNLKK CSGTEASVVAPPPVVLLPDVETPSEEDCMFGNGKGY RGKRATTVTGTPCQDWAAQEPHRHSIFTPETNPRAG LEKNYCRNPDGDVGGPWCYTTNPRKLYDYCDVPQCA APSFDCGKPQVEPKKCPGRWGGCVAHPHSWPWQVSL RTRFGMHFCGGTLISPEWVLTAAHCLEKSPRPSSYK VILGAHQEVNLEPHVQEIEVSRLFLEPTRKDIALLK LSSPAVITDKVIPACLPSPNYVVADRTECFITGWGE TQGTFGAGLLKEAQLPVIENKVCNRYEFLNGRVQST ELCAGHLAGGTDSCQGDSGGPLVCFEKDKYILQGVT SWGLGCARPNKPGVYVRVSRFVTWIEGVMRNN |
| SP domain of hPlm (corresponding to residues 583 to 791) | — | 34 | AAPSFDCGKPQVEPKKCPGRVVGGCVAHPHSWPWQV SLRTRFGMHFCGGTLISPEWVLTAAHCLEKSPRPSS YKVILGAHQEVNLEPHVQEIEVSRLFLEPTRKDIAL LKLSSPAVITDKVIPACLPSPNYVVADRTECFITGW GETQGTFGAGLLKEAQLPVIENKVCNRYEFLNGRVQ STELCAGHLAGGTDSCQGDSGGPLVCFEKDKYILQG VTSWGLGCARPNKPGVYVRVSRFVTWIEGVMRNN His603, Asp646 and Ala/Ser741 form the catalytic triad (shown in bold and underline) |

TABLE 2

Key interactions between B10 antibody and
serine protease (SP) domain of plasmin.

| B10 residue | Distance (Å) | SP residue |
|---|---|---|
| ASP 150 [OD1] | 2.61 | ARG 637 [NH1] |
| SER 149 [O] | 2.71 | ARG 637 [NH1] |
| TYR 222 [OH] | 3.87 | ARG 637 [NH2] |
| ASP 150 [OD2] | 3.12 | LEU 638 [N] |
| TYR 222 [N] | 2.93 | LEU 640 [O] |
| SER 234 [OG] | 2.81 | PRO 642 [O] |
| SER 27 [OG] | 3.58 | ARG 644 [N] |
| GLY 46 [O] | 3.49 | ARG 644 [NE] |
| ASP 48 [OD1] | 3.57 | ARG 644 [NH1] |
| TYR 45 [OH] | 3.40 | LYS 645 [NZ] |
| ASP 48 [OD2] | 3.81 | GLN 721 [NE2] |
| TYR 222 [O] | 2.88 | TRP 783 [NE1] |
| TYR 226 [OH] | 3.16 | ASN 791 [ND2] |
| TYR 222 [OH] | 2.82 | ASN 791 [OD1] |

EXAMPLES

Example 1: Production of B10 Antibody

Antibodies for binding to plasmin were obtained by raised an antibody response in chickens to full length plasminogen. Antibody variable heavy and light chains (VH and VL) were amplified from chicken cDNA by PCR and linked together via a flexible linker to create an scFv library.

Selection was performed by screening for plasminogen-binding antibodies via ELISA and Biacore SK-mediated plasminogen activation and fibrinolytic assays were performed to identify antibodies which prevented or inhibited activation of plasminogen to plasmin or inhibition of plasmin activity.

Example 2: Characterisation of Antibody B10 for
Binding Plasmin Active Site

SPR Assays

Chicken antibodies were immobilised on a series S CM4 (GE healthcare) chip through amine coupling. The binding of plasminogen or plasmin to antibodies of the invention, at concentrations ranging from 0.39 nM to as high as 50 nM was analysed using Biacore T200 (GE Healthcare) in a buffer composed of 10 mM HEPES pH 7.4, 150 mM NaCl, 3 mM EDTA and 0.05% Tween20 in the presence of protease inhibitor cocktail. Plasminogen/plasmin was injected at 30 µl/min for 180 s association, followed by a 600 s dissociation. At the end of each cycle, the sensor chip was regenerated with 10 mM glycine pH 1.8 before the next injection, a minimum of 6 cycles was performed. To obtain kinetic parameters, sensorgrams were fitted with a Langmuir 1:1 binding model using Biacore T200 evaluation software (GE Healthcare).

The results of the binding experiments (FIG. 1), show that an antigen binding protein of the invention binds to both plasminogen and plasmin, but with marginally greater affinity for plasminogen compared to plasmin.

B10 Inhibits the Activity of Plasmin Formed by tPA-Mediated Plasminogen Activation In Solution:

20 nM of plasminogen was mixed with various B10 concentrations (0-200 nM) in the presence of 20 mM EACA for 30 minutes at room temperature. After incubation, plasminogen activation by 4 nM of tPA was measured using fluorogenic substrate (H-Ala-Phe-Lys-AMC, Bachem) in a Fluostar Omega plate reader (BMG Labtech), excitation and emission wavelengths of 355 nm and 460 nm, respectively. The progress curves were fitted to a non-linear exponential equation in GraphPad Prism 6:

$$Y=Y_0*\exp(\text{rate of activation}*X)$$

where $Y_0$ is the Y-value when X=0. The rates of activation were plotted against corresponding B10 concentration to yield an inhibition curve that can be fitted with the inhibitor vs response model in GraphPad Prism 6:

$$Y=Bottom+(Top-Bottom)/(1+((X^{HillSlope})/(IC_{50}^{HillSlope})))$$

where Top and Bottom are plateaus in the fluorescence reading and Hillslope is a measure of the steepness of the curves. The $IC_{50}$ value, i.e., the concentration of B10 that inhibits 50% of tPA-mediated plasminogen activation in solution, is 21.51±2.28 nM.

On Fibrin:

Plasminogen activation was measured on the surface of the preformed fibrin clot, prepared by mixing 3 mg/ml fibrinogen (Banksia Scientific); 1 U of bovine thrombin (Jomar Life Research); and 10 nM of tPA (Boehringer Ingelheim), at 37° C. for 2 hours. 100 nM of plasminogen mixed with B10 at concentrations (0-2 μM) was added to the surface of the clot. Plasmin activity was monitored using 200 μM of fluorogenic substrate (H-Ala-Phe-Lys-AMC, Bachem) as above. The rate of plasminogen activation and $IC_{50}$ were calculated as above. The $IC_{50}$ value obtained for the inhibition of tPA-mediated plasminogen activation on fibrin is 86±11.6 nM. Results are shown in FIG. 2.

B10 Inhibits Activity of Plasmin Formed by SK-Mediated Activation of Plasminogen Plasminogen activation by streptokinase was used to assess the ability of the antibody of the invention. 50 nM of plasminogen was activated with 5 nM of recombinant streptokinase at 37° C. The progress of plasminogen activation was monitored using 200 μM of plasmin fluorogenic substrate H-Ala-Phe-Lys-AMC (Bachem) in a Fluorstar Omega plate reader (BMG Labtech) via excitation and emission wavelengths of 355 nm and 460 nm, respectively. Individually, 0.5 μM of antibody was added at specific time points (t=0, t=60 min and t=160 min) during the process. HEPES-buffered saline was added in place of the antibody as a negative control.

The results in FIG. 3 show that the B10 antibody inhibits plasmin activity instantaneously as it was added to the reaction at any time during the entire course of the assay.

Effect of B10 on the Activity of Plasmin and Other Plasma Proteases

Plasmin (Haematologic Technologies) activity was measured in the presence of 200 μM of fluorogenic substrate (H-Ala-Phe-Lys-AMC, Bachem) in a Fluostar Omega plate reader (BMG Labtech) via excitation and emission wavelengths of 355 nm and 460 nm respectively. Progress curves of B10 and A01 (a non-inhibitory plasminogen antibody) at 10:1 antibody:plasmin ratio. B10 showed complete inhibition of Plm activity compared to A01. The activity of plasmin (20 nM) in the presence of the antibody B10 (0-200 nM) was measured at 37° C. using a Fluostar Omega plate reader (BMG Labtech) via excitation and emission wavelengths of 355 nm and 460 nm, respectively. The $IC_{50}$ was determined to be 24.3±1.4 nM.

Figure 4C:
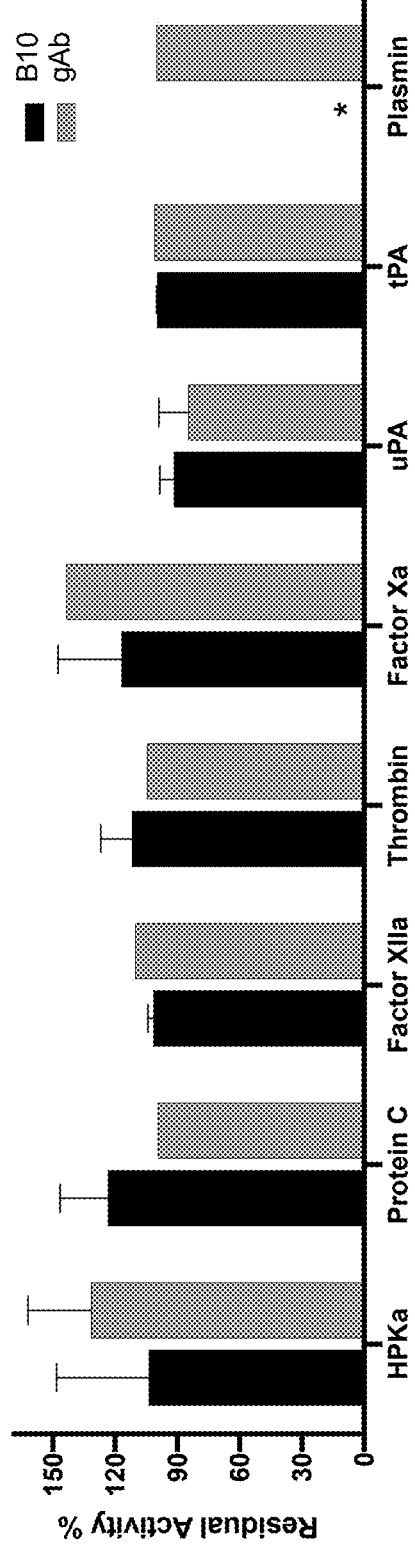
FIG. 4: Effect of B10 on enzyme activity of plasmin and other serine proteases. (A) Progress curves of plasmin activity in the presence of B10 or a non-inhibitory plasminogen-binding antibody (A01). Plasmin activity was not detectable in the presence of B10. (B) Plasmin activity was assayed in the presence of B10 (0-100 nM), the $IC_{50}$ is 24.3±1.4 nM; total inhibition was recorded at plasmin to B10 of 1:10 ratio. (C) Apart from plasmin (*), B10 does not inhibit the enzyme activity of serine proteases including human activated kallikrein (HPKa), protein C, factor XIIa, thrombin, factor Xa, uPA and tPA. Also shown is activity of the enzymes in the presence of the naive antibody gAb.

To test for cross-reactivity to other plasma serine proteases, 250 nM of B10 was mixed with 10 nM of human plasma proteases namely plasma kallikrein (Molecular Innovations), factor Xa (Molecular Innovations), factor XIIa (Enzyme research laboratories), protein C (Molecular Innovations), thrombin (Molecular Innovations), uPA (Abbokinase), tPA (Actilyse) and plasmin. Thrombin, Factor Xa, tPA and plasmin activity were measured using chromogenic substrate T2943 (Sigma Aldrich) whereas plasma kallikrein, factor XIIa and protein C activity were measured using chromogenic substrate S2032 (Chromogenix) at 37° C. using a Fluostar Omega plate reader (BMG Labtech) at 405 nm. uPA activity was measured using fluorogenic substrate (Spectrofluor) at 37° C. using a Fluostar Omega plate reader (BMG Labtech) via excitation and emission wavelengths of 355 nm and 460 nm, respectively. The activity of the enzymes in the presence of the naïve antibody gAb is also shown. Here, the enzyme activity was normalised against the HEPES-buffered saline control where the antibody is substituted with the buffer. As shown in FIG. 4C, B10 has no effect on the activity on the plasma proteases tested apart from Plm.

Inhibition of SK-Binding to Plasminogen by B10

The impact of B10 on binding of streptokinase to plasminogen was investigated using Biacore T200 (GE Healthcare). 10 nM plasminogen was passed over streptokinase immobilized on a CM4 (GE Healthcare) chip in the presence of B10 or a naïve chicken antibody (gAb), at 0, 62.5, 125, 250 and 500 nM. B10 showed inhibition at all concentrations 62.5-500 nM tested. Naïve chicken antibody gAb, the control, showed no inhibition. In FIG. 5B, the percentage of SK binding (normalized against to no antibody control) to plasminogen in the presence of 500 nM G05 and gAb is shown.

The result, shown in FIG. 5, indicates that B10 inhibits plasminogen binding to streptokinase by ~33% compared with the control antibody.

Example 3: Binding of B10 to the Serine Protease Domain

Figure 6:
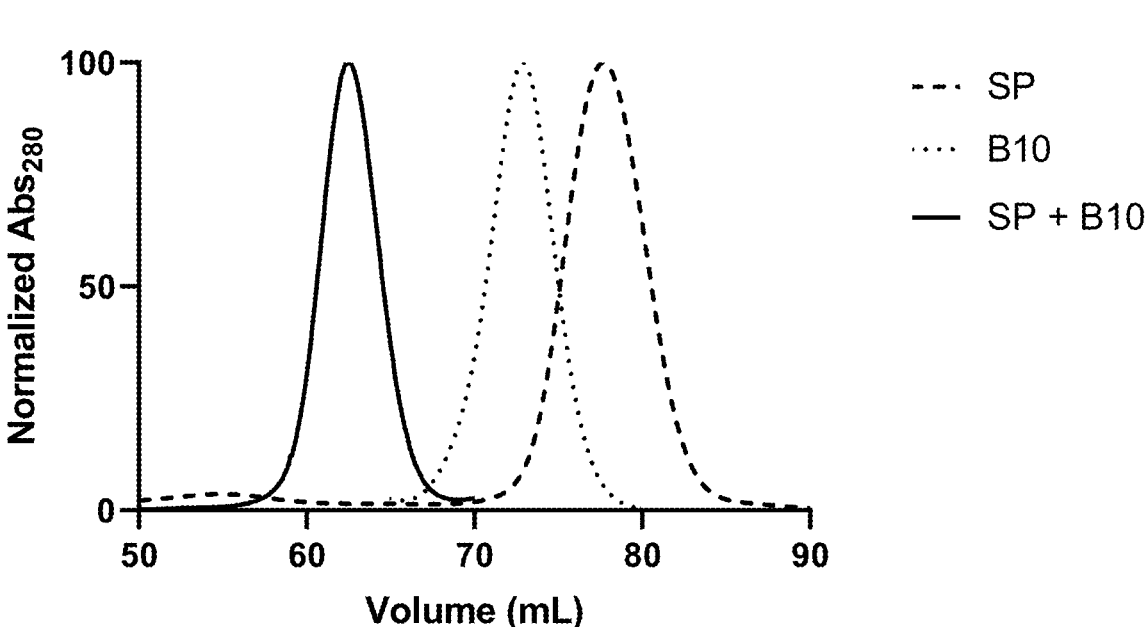
FIG. 6: B10 binding to a single recombinant serine protease domain. Size exclusion chromatography shows a higher molecular weight complex (SP+B10, solid line) compared to SP alone (dashed line) or B10 alone (dotted line).

B10 binds to and forms stable binary complex with kringle 5-serine protease domain (KR5-SP) that can be co-purified by size-exclusion chromatography. A Superdex 200 16/60 column (GE Healthcare) was used and the buffer was HEPES-buffered saline. As shown in FIG. 6, the co-complex was eluted at 58.5 ml as a single peak. As a reference, the KR5-SP and B10 antibody was eluted at 67.2 ml and 73.3 ml, respectively, also as a single peak.

Example 4: Crystal Structure of B10 Binding to Single Recombinant Kringle 5-Serine Protease Domain The purified complex at 10 mg/ml in a buffer containing 25 mM HEPES, 150 mM NaCl was crystallized the presence of 0.1 M MES pH 6.5 and 0.2 M $(NH_4)_2SO_4$, 20% (w/v) PEG 8K at 20° C. Crystals were flash cooled in liquid N2 in the presence of 20% (v/v) glycerol. A 2.7 Å dataset was collected at the Australian Synchrotron MX2 beamline using the EIGER X 16M pixel detector (Dectris Ltd, Switzerland also known as the ACRF detector). The crystal structure was solved using the program PHASER (CCP4) by molecular replacement, using the SP domain from the structure of plasminogen (PDB ID 4DUR) and chicken single-chain fragment variable (PDB ID 4P48) as search models. Multiple rounds of modelling using COOT and refinement using PHENIX was performed. The final model was shown in FIG. 7 prepared using PyMOL (www.pymol.org/).

The B10-SP complex structure reveals that binding of B110 to the catalytic domain interferes with the formation of a functional catalytic site, such that it prevents plasmin binding to/cleaving of substrates.

Example 5: Effect of B10 on Plasmin Activity in the Presence of GAS

GAS culture was grown as above but to the $OD_{600}$ of 1.0. 1 ml of culture was used for each sample. Cells were washed twice, and each sample was resuspended in 250 μl of PBS supplemented with 2% plasminogen-depleted FCS. 80 nM of plasminogen and 8 μM of B10/gAb or 13.5 mM TXA were mixed for 15 minutes at room temperature followed by incubation with the washed GAS cells for 1 hour at room temperature. After the 1-hour incubation, cells were washed twice and finally resuspended in 50 μl of of PBS supplemented with 2% plasminogen-depleted FCS. 10 μl of the resuspended cells was added to a 100 μl reaction mixture buffered with 25 mM Tris, 150 mM NaCl, 0.05% Tween20 pH 7.4 and 200 μM fluorogenic substrate H-Ala-Phe-Lys-AMC (Bachem). Plasmin activity was measured at 37° C. in a Fluorstar Omega plate reader (BMG labtech) via excitation and emission wavelengths of 355 nm and 460 nm respectively.

The result, shown in FIG. 8, shows that B10 reduces plasmin activity generated by GAS by about 60% compared to the control antibody and HEPES-buffered saline control. The bottom panel illustrates that in the absence of GAS cells, recombinant SK (2 nM) activates Plg in solution.

Example 6: B10 Inhibits Lysis of Synthetic Clots and Whole Blood Clots

Synthetic fibrin clots were formed by mixing 3 mg/ml fibrinogen (Banksia Scientific); 1 U of bovine thrombin (Jomar Life Research); and 10 nM of tPA (Boehringer Ingelheim), at 37° C. for 2 hours. Fibrinolysis was initiated by addition of 45 nM of plasminogen mixed with 0-90 nM B10; or 0-90 nM α2AP; or 0-6.25 mM TXA, to the surface of the clot.

Figure 9:
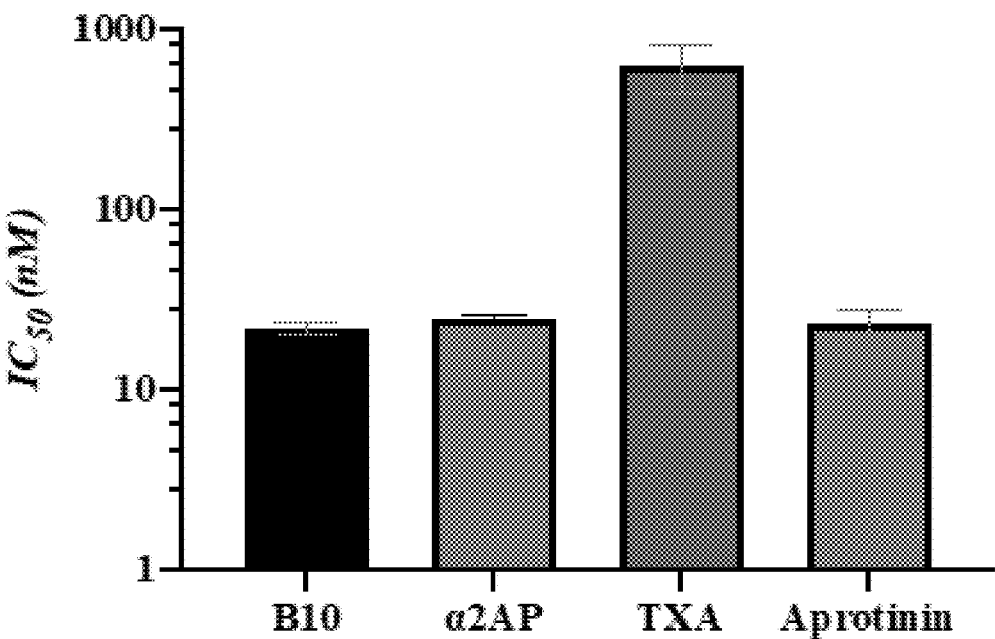
FIG. 9: B10 inhibits fibrinolysis of synthetic clots. Fibrinolysis was measured on preformed fibrin clots, prepared by mixing 3 mg/ml fibrinogen, 1 U of bovine thrombin; and 10 nM of tPA, at 37° C. for 2 hours. 45 nM of plasminogen was mixed with 0-90 nM B110; or $\alpha 2AP$; or 0-6.25 mM TXA, and added to the surface of the clot. Fibrinolysis was monitored on a Nephelometer at 37° C. for up to 10 hours. The time required to achieve 50% clot lysis was used for $IC_{50}$ calculation. The $IC_{50}$ value obtained for B10 is comparable to that of the $\alpha 2AP$ and Aprotinin.

Fibrinolysis was monitored on a Nephelometer (BMG) at 37° C. for up to 10 hours. The time required to achieve 50% clot lysis was used for $IC_{50}$ calculation. The $IC_{50}$ value obtained for B10 is comparable to that of the α2AP and Aprotinin (FIG. 9), and significantly lower (approximately 50-fold) than for TXA.

Whole blood clots were formed from human blood collected from healthy donors. Halo-shaped clots were generated by mixing whole blood with 15% of a mixture containing recombinant tissue factor supplemented with synthetic phospholipids Dade Innovin, Siemens Germany and 67 mM $CaCl_2$ in HBS at 1:4 ratio. The plate was sealed and incubated at 37° C. for 60 min before use.

Clot lysis was induced by the addition of tPA to 7 nM and antibodies or Plm inhibitors at the following concentrations: 0-312.5 nM B10; 0-1000 nM α2AP; 0-1000 nM aprotinin; 0-7.5 mM TXA. Clot lysis leads to an increase of turbidity and was monitored at $OD6_{10}$ nm using a plate reader.

At high concentrations (e.g. up to 1,000 nM), α2AP and Aprotinin only partially inhibit clot lysis; TXA at a concentration up to 100 μM delayed clot lysis and total inhibition of clot lysis was observed at 300 μM and above (data not shown). Antibody B10 completely inhibits clot lysis at concentrations of 250 nM and above.

Figure 10:
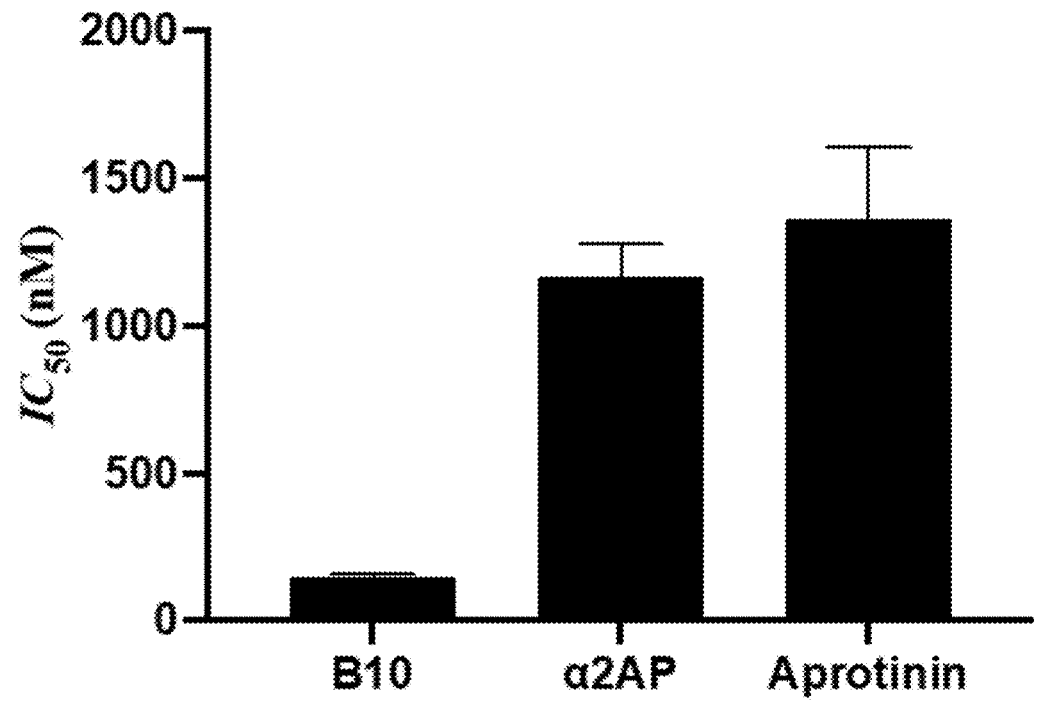
FIG. 10: B10 inhibits whole blood clot lysis in the presence of red blood cells and platelets. The percentage of clot lysis (in comparison to the negative and positive control) is shown as a function of the inhibitor concentration at the time point (30-40 minutes) that achieved full lysis in the positive control, and is plotted using nonlinear regression to calculate the $IC_{50}$. B110 is approximately 8-fold more efficacious than $\alpha 2AP$ and approximately 9-fold more efficacious than Aprotinin in inhibiting whole blood clot lysis.

The time required to achieve 50% clot lysis was used for $IC_{50}$ calculation. The $IC_{50}$ value obtained for B10 was approximately 8-fold higher than for α2AP and approximately 9.5-fold higher than Aprotinin (FIG. 10), indicating that B10 is significantly more efficacious at inhibiting whole blood clot lysis. B10 was more than 180-fold more efficacious than TXA (not shown).

Thus, in the context of a clot lysis assay which closely resembles a physiological system, antibody B10 is significantly more effective than the physiological inhibitor of plasmin, α2AP, at inhibiting plasmin-induced lysis. Further, antibody B10 is significantly more effective than existing pharmacological agents, TXA and Aprotinin at inhibiting plasmin-induced lysis.

It will be understood that the invention disclosed and defined in this specification extends to all alternative combinations of two or more of the individual features mentioned or evident from the text or drawings. All of these different combinations constitute various alternative aspects of the invention.

---

The invention claimed is:

1. An antigen binding protein comprising an antigen binding domain that binds to the serine protease domain of plasmin, wherein the antigen binding domain comprises:

(a) a VH comprising a CDR1 comprising the sequence set forth in SEQ ID NO: 4, a CDR2 comprising the sequence set forth between in SEQ ID NO: 5 and a CDR3 comprising the sequence set forth in SEQ ID NO: 6, and (b) a VL comprising a CDR1 comprising the sequence set forth in SEQ ID NO: 1, a CDR2 comprising the sequence set forth in SEQ ID NO: 2 and a CDR3 comprising the sequence set forth in SEQ ID NO: 3.

2. The antigen binding protein of claim 1, wherein the protein further comprises at least one of:

(i) a VH comprising a framework region (FR) 1 comprising a sequence at least about 80%, at least 85%, at least 90%, at least 92%, at least 95%, at least 97%, at least 99% identical to the sequence set forth in SEQ ID NO: 21, a FR2 comprising a sequence at least about 80%, at least 85%, at least 90%, at least 92%, at least 95%, at least 97%, at least 99% identical to the sequence set forth in SEQ ID NO: 22, a FR3 comprising a sequence at least about 80%, at least 85%, at least 90%, at least 92%, at least 95%, at least 97%, at least 99% identical to the sequence set forth in SEQ ID NO: 23, and a FR4 comprising a sequence at least about 80%, at least 85%, at least 90%, at least 92%, at least 95%, at least 97%, at least 99% identical to the sequence set forth in SEQ ID NO: 24;

(ii) a VL comprising a FR1 comprising a sequence at least about 80%, at least 85%, at least 90%, at least 92%, at least 95%, at least 97%, at least 99% identical to the sequence set forth in SEQ ID NO: 17, a FR2 comprising a sequence at least about 80%, at least 85%, at least 90%, at least 92%, at least 95%, at least 97%, at least 99% identical to the sequence set forth in SEQ ID NO: 18, a FR3 comprising a sequence at least about 80%, at least 85%, at least 90%, at least 92%, at least 95%, at least 97%, at least 99% identical to the sequence set forth in SEQ ID NO: 19, and a FR4 comprising a sequence at least about 80%, at least 85%, at least 90%, at least 92%, at least 95%, at least 97%, at least 99% identical to the sequence set forth in SEQ ID NO: 20;

(iii) a VH comprising a FR1 comprising the sequence set forth in SEQ ID NO: 21, a FR2 comprising the sequence set forth between in SEQ ID NO: 22, a FR3 comprising the sequence set forth in SEQ ID NO: 23, and a FR4 comprising the sequence set forth in SEQ ID NO: 24;

(iv) a VL comprising a FR1 comprising the sequence set forth in SEQ ID NO: 17, a FR2 comprising the sequence set forth between in SEQ ID NO: 18, a FR3 comprising the sequence set forth in SEQ ID NO: 19, and a FR4 comprising the sequence set forth in SEQ ID NO: 20; or (v) a VH comprising a FR1 comprising the sequence set forth in SEQ ID NO: 21, a FR2 comprising the sequence set forth between in SEQ ID NO: 22, a FR3 comprising the sequence set forth in SEQ ID NO: 23, and a FR4 comprising the sequence set forth in SEQ ID NO: 24; and a VL comprising a FR1 comprising the sequence set forth in SEQ ID NO: 17, a FR2 comprising the sequence set forth between in SEQ ID NO: 18, a FR3 comprising the sequence set forth in SEQ ID NO: 19, and a FR4 comprising the sequence set forth in SEQ ID NO: 20.

3. The antigen binding protein of claim 1, wherein the antigen binding protein is in the form of:

(i) a single chain Fv fragment (scFv);

(ii) a dimeric scFv (di-scFv);

(iii) one of (i) or (ii) linked to a constant region of an antibody, Fc or a heavy chain constant domain (CH) 2 and/or CH3;

(iv) one of (i) or (ii) linked to a protein that binds to an immune effector cell;

(v) an antibody;

(vi) a diabody;

(vii) a triabody;

(viii) a tetrabody;

(ix) a Fab;

(x) a F (ab')2;

(xi) a Fv;

(xii) a bispecific antibody;

(xiii) one of (vi) to (xii) linked to a constant region of an antibody, Fc or a heavy chain constant domain (CH) 2 and/or CH3; or (xiv) one of (vi) to (xiii) linked to a protein that binds to an immune effector cell.

4. The antigen binding protein of claim 1, wherein the VH and VL are joined by a linker, wherein the linker is a chemical, one or more amino acids, or a disulphide bond formed between two cysteine residues.

5. The antigen binding protein of claim 1, wherein the protein is in the form of a fusion protein comprising an antigen binding protein of claim 1.

6. A conjugate comprising an antigen binding protein of claim 1, conjugated to a label or a cytotoxic agent.

7. A pharmaceutical composition comprising an antigen binding protein of claim 1, or a fusion protein or conjugate thereof, and a pharmaceutically acceptable excipient.

8. The antigen binding protein of claim 1, wherein the antigen binding domain comprises a VH comprising a sequence at least about 95% or 96% or 97% or 98% or 99% identical to the sequence set forth in SEQ ID NO: 8.

9. The antigen binding protein of claim 1, wherein the antigen binding domain comprises a VH comprising the sequence set forth in SEQ ID NO: 8.

10. The antigen binding protein of claim 1, wherein the antigen binding domain comprises a VL comprising a sequence at least about 95% or 96% or 97% or 98% or 99% identical to the sequence set forth in SEQ ID NO: 7.

11. The antigen binding protein of claim 1, wherein the antigen binding domain comprises a VL comprising the sequence set forth in SEQ ID NO: 7.

12. The antigen binding protein of claim 1, wherein the antigen binding domain comprises a VH comprising the sequence set forth in SEQ ID NO: 8 and a VL comprising the sequence set forth in SEQ ID NO: 7.

13. The antigen binding protein of claim 3, wherein the antigen binding protein is in the form of a monoclonal antibody.

* * * * *

SEQUENCE LISTING

```
<160> NUMBER OF SEQ ID NOS: 34

<210> SEQ ID NO 1
<211> LENGTH: 4
<212> TYPE: PRT
<213> ORGANISM: Artificial Sequence
<220> FEATURE:
<223> OTHER INFORMATION: Antibody B10, LCDR1 (protein)

<400> SEQUENCE: 1

Asp Ser Gly Ser
1

<210> SEQ ID NO 2
<211> LENGTH: 3
<212> TYPE: PRT
<213> ORGANISM: Artificial Sequence
<220> FEATURE:
<223> OTHER INFORMATION: Antibody B10, LCDR2 (protein)

<400> SEQUENCE: 2

Gly Ser Asp
1

<210> SEQ ID NO 3
<211> LENGTH: 9
```

```
<212> TYPE: PRT
<213> ORGANISM: Artificial Sequence
<220> FEATURE:
<223> OTHER INFORMATION: Antibody B10, LCDR3 (protein)

<400> SEQUENCE: 3

Gly Thr Ala Asp Ser Ser Thr Thr Ala
1               5

<210> SEQ ID NO 4
<211> LENGTH: 8
<212> TYPE: PRT
<213> ORGANISM: Artificial Sequence
<220> FEATURE:
<223> OTHER INFORMATION: Antibody B10, HCDR1 (protein)

<400> SEQUENCE: 4

Gly Phe Ile Phe Ser Asp Tyr Gly
1               5

<210> SEQ ID NO 5
<211> LENGTH: 8
<212> TYPE: PRT
<213> ORGANISM: Artificial Sequence
<220> FEATURE:
<223> OTHER INFORMATION: Antibody B10, HCDR2 (protein)

<400> SEQUENCE: 5

Ile Asp Asp Asp Gly Gly Gly Thr
1               5

<210> SEQ ID NO 6
<211> LENGTH: 21
<212> TYPE: PRT
<213> ORGANISM: Artificial Sequence
<220> FEATURE:
<223> OTHER INFORMATION: Antibody B10, HCDR3 (protein)

<400> SEQUENCE: 6

Ala Lys Ala Val Gly Tyr Gly Cys Thr Tyr Leu Gly Tyr Ser Cys Ala
1               5                   10                  15

Gly Ser Ile Asp Ala
            20

<210> SEQ ID NO 7
<211> LENGTH: 103
<212> TYPE: PRT
<213> ORGANISM: Artificial Sequence
<220> FEATURE:
<223> OTHER INFORMATION: Antibody B10, VL (protein)

<400> SEQUENCE: 7

Gln Ala Ala Leu Thr Gln Pro Ser Ser Val Ser Ala Asn Pro Gly Glu
1               5                   10                  15

Thr Val Lys Ile Thr Cys Ser Gly Gly Asp Ser Gly Ser Tyr Gly Trp
            20                  25                  30

Tyr Gln Gln Lys Ala Pro Gly Ser Ala Pro Val Thr Val Ile Tyr Gly
        35                  40                  45

Ser Asp Lys Arg Pro Ser Asp Ile Pro Ser Arg Phe Ser Gly Ser Thr
    50                  55                  60

Ser Gly Ser Thr Asn Thr Leu Thr Ile Thr Gly Val Gln Val Glu Asp
65                  70                  75                  80

Glu Ala Ile Tyr Tyr Cys Gly Thr Ala Asp Ser Ser Thr Thr Ala Ala
                85                  90                  95
```

-continued

```
Gly Thr Thr Leu Thr Val Leu
            100

<210> SEQ ID NO 8
<211> LENGTH: 129
<212> TYPE: PRT
<213> ORGANISM: Artificial Sequence
<220> FEATURE:
<223> OTHER INFORMATION: Antibody B10, VH (protein)

<400> SEQUENCE: 8

Ala Val Thr Leu Asp Glu Ser Gly Gly Gly Leu Gln Thr Pro Gly Gly
1               5                   10                  15

Ala Leu Ser Leu Val Cys Lys Gly Ser Gly Phe Ile Phe Ser Asp Tyr
            20                  25                  30

Gly Met Phe Trp Val Arg Gln Ala Pro Gly Lys Gly Leu Glu Trp Val
        35                  40                  45

Ala Gly Ile Asp Asp Asp Gly Gly Gly Thr Ser Tyr Tyr Ala Pro Ala
    50                  55                  60

Val Lys Gly Arg Ala Thr Ile Ser Arg Asp Asn Gly Gln Ser Thr Val
65                  70                  75                  80

Arg Leu Gln Leu Asn Asn Leu Arg Ala Glu Asp Thr Gly Thr Tyr Tyr
                85                  90                  95

Cys Ala Lys Ala Val Gly Tyr Gly Cys Thr Tyr Leu Gly Tyr Ser Cys
            100                 105                 110

Ala Gly Ser Ile Asp Ala Trp Gly His Gly Thr Glu Val Ile Val Ser
        115                 120                 125

Ser

<210> SEQ ID NO 9
<211> LENGTH: 12
<212> TYPE: DNA
<213> ORGANISM: Artificial Sequence
<220> FEATURE:
<223> OTHER INFORMATION: Antibody B10, LCDR1 (DNA)

<400> SEQUENCE: 9
gatagcggct cc                                                    12

<210> SEQ ID NO 10
<211> LENGTH: 9
<212> TYPE: DNA
<213> ORGANISM: Artificial Sequence
<220> FEATURE:
<223> OTHER INFORMATION: Antibody B10, LCDR2 (DNA)

<400> SEQUENCE: 10 ggctctgat                                                         9

<210> SEQ ID NO 11
<211> LENGTH: 28
<212> TYPE: DNA
<213> ORGANISM: Artificial Sequence
<220> FEATURE:
<223> OTHER INFORMATION: Antibody B10, LCDR3 (DNA)

<400> SEQUENCE: 11
ggcaccgccg actctagcac cacagccg                                   28

<210> SEQ ID NO 12
<211> LENGTH: 24
```

```
<212> TYPE: DNA
<213> ORGANISM: Artificial Sequence
<220> FEATURE:
<223> OTHER INFORMATION: Antibody B10, HCDR1 (DNA)

<400> SEQUENCE: 12
ggcttcatct tttctgacta cgga                                                24

<210> SEQ ID NO 13
<211> LENGTH: 27
<212> TYPE: DNA
<213> ORGANISM: Artificial Sequence
<220> FEATURE:
<223> OTHER INFORMATION: Antibody B10, HCDR2 (DNA)

<400> SEQUENCE: 13
atcgacgatg acggaggagg cacctcc                                             27

<210> SEQ ID NO 14
<211> LENGTH: 63
<212> TYPE: DNA
<213> ORGANISM: Artificial Sequence
<220> FEATURE:
<223> OTHER INFORMATION: Antibody B10, HCDR3 (DNA)

<400> SEQUENCE: 14
gccaaggccg tgggctatgg ctgcacatac ctgggctatt cttgtgcagg cagcatcgac      60
gca                                                                       63

<210> SEQ ID NO 15
<211> LENGTH: 309
<212> TYPE: DNA
<213> ORGANISM: Artificial Sequence
<220> FEATURE:
<223> OTHER INFORMATION: Antibody B10, VL (DNA)

<400> SEQUENCE: 15
caggccgcac tgacccagcc tagctccgtg agcgccaacc caggcgagac agtgaagatc      60
acatgctccg gaggcgatag cggctcctac ggctggtatc agcagaaggc ccccggctcc     120
gcccctgtga ccgtgatcta cggctctgat aagcggccaa cgcacatccc ctcccgcttc     180
tctggcagca catccggctc taccaataca ctgaccatca caggcgtgca ggtggaggat     240
gaggccatct actattgcgg caccgccgac tctagcacca cagccgccgg caccacactg     300
acagtgctg                                                               309

<210> SEQ ID NO 16
<211> LENGTH: 387
<212> TYPE: DNA
<213> ORGANISM: Artificial Sequence
<220> FEATURE:
<223> OTHER INFORMATION: Antibody B10, VH (DNA)

<400> SEQUENCE: 16
gccgtgaccc tggatgagag cggaggaggc ctccagacac ccggcggcgc cctgagcctg      60
gtgtgcaagg ctccggctt catcttttct gactacggaa tgttttgggt gcgccaggcc     120
cccggcaagg gcctggagtg ggtggcagga atcgacgatg acggaggagg cacctcctac     180
tatgcacctg ccgtgaaggg aaaggcaacc atcagcagag ataacggcca gagcaccgtg     240
aggctccagc tgaacaatct gagagccgag gacaccggca catactattg tgccaaggcc     300
gtgggctatg gctgcacata cctgggctat tcttgtgcag gcagcatcga cgcatggggc     360
```

-continued cacggcaccg aagtgatcgt gagcagc 387

```
<210> SEQ ID NO 17
<211> LENGTH: 25
<212> TYPE: PRT
<213> ORGANISM: Artificial Sequence
<220> FEATURE:
<223> OTHER INFORMATION: Antibody B10, LFR1 (protein)

<400> SEQUENCE: 17

Gln Ala Ala Leu Thr Gln Pro Ser Ser Val Ser Ala Asn Pro Gly Glu
1               5                   10                  15

Thr Val Lys Ile Thr Cys Ser Gly Gly
            20                  25

<210> SEQ ID NO 18
<211> LENGTH: 18
<212> TYPE: PRT
<213> ORGANISM: Artificial Sequence
<220> FEATURE:
<223> OTHER INFORMATION: Antibody B10, LFR2 (protein)

<400> SEQUENCE: 18

Tyr Gly Trp Tyr Gln Gln Lys Ala Pro Gly Ser Ala Pro Val Thr Val
1               5                   10                  15

Ile Tyr

<210> SEQ ID NO 19
<211> LENGTH: 36
<212> TYPE: PRT
<213> ORGANISM: Artificial Sequence
<220> FEATURE:
<223> OTHER INFORMATION: Antibody B10, LFR3 (protein)

<400> SEQUENCE: 19

Lys Arg Pro Ser Asp Ile Pro Ser Arg Phe Ser Gly Ser Thr Ser Gly
1               5                   10                  15

Ser Thr Asn Thr Leu Thr Ile Thr Gly Val Gln Val Glu Asp Glu Ala
            20                  25                  30

Ile Tyr Tyr Cys
        35

<210> SEQ ID NO 20
<211> LENGTH: 8
<212> TYPE: PRT
<213> ORGANISM: Artificial Sequence
<220> FEATURE:
<223> OTHER INFORMATION: Antibody B10, LFR4 (protein)

<400> SEQUENCE: 20

Ala Gly Thr Thr Leu Thr Val Leu
1               5

<210> SEQ ID NO 21
<211> LENGTH: 25
<212> TYPE: PRT
<213> ORGANISM: Artificial Sequence
<220> FEATURE:
<223> OTHER INFORMATION: Antibody B10, HFR1 (protein)

<400> SEQUENCE: 21

Ala Val Thr Leu Asp Glu Ser Gly Gly Gly Leu Gln Thr Pro Gly Gly
1               5                   10                  15

Ala Leu Ser Leu Val Cys Lys Gly Ser
```

```
                    20              25
```

```
<210> SEQ ID NO 22
<211> LENGTH: 17
<212> TYPE: PRT
<213> ORGANISM: Artificial Sequence
<220> FEATURE:
<223> OTHER INFORMATION: Antibody B10, HFR2 (protein)

<400> SEQUENCE: 22

Met Phe Trp Val Arg Gln Ala Pro Gly Lys Gly Leu Glu Trp Val Ala
1               5                   10                  15

Gly
```

```
<210> SEQ ID NO 23
<211> LENGTH: 39
<212> TYPE: PRT
<213> ORGANISM: Artificial Sequence
<220> FEATURE:
<223> OTHER INFORMATION: Antibody B10, HFR3 (protein)

<400> SEQUENCE: 23

Ser Tyr Tyr Ala Pro Ala Val Lys Gly Arg Ala Thr Ile Ser Arg Asp
1               5                   10                  15

Asn Gly Gln Ser Thr Val Arg Leu Gln Leu Asn Asn Leu Arg Ala Glu
            20                  25                  30

Asp Thr Gly Thr Tyr Tyr Cys
        35
```

```
<210> SEQ ID NO 24
<211> LENGTH: 11
<212> TYPE: PRT
<213> ORGANISM: Artificial Sequence
<220> FEATURE:
<223> OTHER INFORMATION: Antibody B10, HFR4 (protein)

<400> SEQUENCE: 24

Trp Gly His Gly Thr Glu Val Ile Val Ser Ser
1               5                   10
```

```
<210> SEQ ID NO 25
<211> LENGTH: 75
<212> TYPE: DNA
<213> ORGANISM: Artificial Sequence
<220> FEATURE:
<223> OTHER INFORMATION: Antibody B10, LFR1 (DNA)

<400> SEQUENCE: 25
caggccgcac tgacccagcc tagctccgtg agcgccaacc caggcgagac agtgaagatc      60
acatgctccg gaggc                                                       75
```

```
<210> SEQ ID NO 26
<211> LENGTH: 54
<212> TYPE: DNA
<213> ORGANISM: Artificial Sequence
<220> FEATURE:
<223> OTHER INFORMATION: Antibody B10, LFR2 (DNA)

<400> SEQUENCE: 26
tacggctggt atcagcagaa ggccccccggc tccgcccctg tgaccgtgat ctac            54
```

```
<210> SEQ ID NO 27
<211> LENGTH: 108
<212> TYPE: DNA
```

-continued

```
<213> ORGANISM: Artificial Sequence
<220> FEATURE:
<223> OTHER INFORMATION: Antibody B10, LFR3 (DNA)

<400> SEQUENCE: 27
aagcggccaa gcgacatccc ctcccgcttc tctggcagca catccggctc taccaataca      60
ctgaccatca caggcgtgca ggtggaggat gaggccatct actattgc                   108

<210> SEQ ID NO 28
<211> LENGTH: 24
<212> TYPE: DNA
<213> ORGANISM: Artificial Sequence
<220> FEATURE:
<223> OTHER INFORMATION: Antibody B10, LFR4 (DNA)

<400> SEQUENCE: 28
gccggcacca cactgacagt gctg                                             24

<210> SEQ ID NO 29
<211> LENGTH: 75
<212> TYPE: DNA
<213> ORGANISM: Artificial Sequence
<220> FEATURE:
<223> OTHER INFORMATION: Antibody B10, HFR1 (DNA)

<400> SEQUENCE: 29
gccgtgaccc tggatgagag cggaggaggc ctccagacac ccggcggcgc cctgagcctg      60
gtgtgcaagg gctcc                                                      75

<210> SEQ ID NO 30
<211> LENGTH: 51
<212> TYPE: DNA
<213> ORGANISM: Artificial Sequence
<220> FEATURE:
<223> OTHER INFORMATION: Antibody B10, HFR2 (DNA)

<400> SEQUENCE: 30
atgttttggg tgcgccaggc ccccggcaag ggcctggagt gggtggcagg a               51

<210> SEQ ID NO 31
<211> LENGTH: 117
<212> TYPE: DNA
<213> ORGANISM: Artificial Sequence
<220> FEATURE:
<223> OTHER INFORMATION: Antibody B10, HFR3 (DNA)

<400> SEQUENCE: 31
tcctactatg cacctgccgt gaagggaagg gcaaccatca gcagagataa cggccagagc      60
accgtgaggc tccagctgaa caatctgaga gccgaggaca ccggcacata ctattgt        117

<210> SEQ ID NO 32
<211> LENGTH: 33
<212> TYPE: DNA
<213> ORGANISM: Artificial Sequence
<220> FEATURE:
<223> OTHER INFORMATION: Antibody B10, HFR4 (DNA)

<400> SEQUENCE: 32
tggggccacg gcaccgaagt gatcgtgagc agc                                   33

<210> SEQ ID NO 33
<211> LENGTH: 791
<212> TYPE: PRT
<213> ORGANISM: Homo sapiens
```

-continued

```
<400> SEQUENCE: 33

Glu Pro Leu Asp Asp Tyr Val Asn Thr Gln Gly Ala Ser Leu Phe Ser
1               5                   10                  15

Val Thr Lys Lys Gln Leu Gly Ala Gly Ser Ile Glu Glu Cys Ala Ala
            20                  25                  30

Lys Cys Glu Glu Asp Glu Glu Phe Thr Cys Arg Ala Phe Gln Tyr His
        35                  40                  45

Ser Lys Glu Gln Gln Cys Val Ile Met Ala Glu Asn Arg Lys Ser Ser
        50                  55                  60

Ile Ile Ile Arg Met Arg Asp Val Val Leu Phe Glu Lys Lys Val Tyr
65                  70                  75                  80

Leu Ser Glu Cys Lys Thr Gly Asn Gly Lys Asn Tyr Arg Gly Thr Met
                85                  90                  95

Ser Lys Thr Lys Asn Gly Ile Thr Cys Gln Lys Trp Ser Ser Thr Ser
            100                 105                 110

Pro His Arg Pro Arg Phe Ser Pro Ala Thr His Pro Ser Glu Gly Leu
            115                 120                 125

Glu Glu Asn Tyr Cys Arg Asn Pro Asp Asn Asp Pro Gln Gly Pro Trp
            130                 135                 140

Cys Tyr Thr Thr Asp Pro Glu Lys Arg Tyr Asp Tyr Cys Asp Ile Leu
145                 150                 155                 160

Glu Cys Glu Glu Glu Cys Met His Cys Ser Gly Glu Asn Tyr Asp Gly
                165                 170                 175

Lys Ile Ser Lys Thr Met Ser Gly Leu Glu Cys Gln Ala Trp Asp Ser
            180                 185                 190

Gln Ser Pro His Ala His Gly Tyr Ile Pro Ser Lys Phe Pro Asn Lys
            195                 200                 205

Asn Leu Lys Lys Asn Tyr Cys Arg Asn Pro Asp Arg Glu Leu Arg Pro
            210                 215                 220

Trp Cys Phe Thr Thr Asp Pro Asn Lys Arg Trp Glu Leu Cys Asp Ile
225                 230                 235                 240

Pro Arg Cys Thr Thr Pro Pro Pro Ser Ser Gly Pro Thr Tyr Gln Cys
                245                 250                 255

Leu Lys Gly Thr Gly Glu Asn Tyr Arg Gly Asn Val Ala Val Thr Val
            260                 265                 270

Ser Gly His Thr Cys Gln His Trp Ser Ala Gln Thr Pro His Thr His
            275                 280                 285

Asn Arg Thr Pro Glu Asn Phe Pro Cys Lys Asn Leu Asp Glu Asn Tyr
            290                 295                 300

Cys Arg Asn Pro Asp Gly Lys Arg Ala Pro Trp Cys His Thr Thr Asn
305                 310                 315                 320

Ser Gln Val Arg Trp Glu Tyr Cys Lys Ile Pro Ser Cys Asp Ser Ser
                325                 330                 335

Pro Val Ser Thr Glu Gln Leu Ala Pro Thr Ala Pro Pro Glu Leu Thr
            340                 345                 350

Pro Val Val Gln Asp Cys Tyr His Gly Asp Gly Gln Ser Tyr Arg Gly
            355                 360                 365

Thr Ser Ser Thr Thr Thr Thr Gly Lys Lys Cys Gln Ser Trp Ser Ser
            370                 375                 380

Met Thr Pro His Arg His Gln Lys Thr Pro Glu Asn Tyr Pro Asn Ala
385                 390                 395                 400

Gly Leu Thr Met Asn Tyr Cys Arg Asn Pro Asp Ala Asp Lys Gly Pro
```

-continued

```
                  405              410              415

Trp Cys Phe Thr Thr Asp Pro Ser Val Arg Trp Glu Tyr Cys Asn Leu
            420              425              430

Lys Lys Cys Ser Gly Thr Glu Ala Ser Val Val Ala Pro Pro Pro Val
            435              440              445

Val Leu Leu Pro Asp Val Glu Thr Pro Ser Glu Glu Asp Cys Met Phe
        450              455              460

Gly Asn Gly Lys Gly Tyr Arg Gly Lys Arg Ala Thr Thr Val Thr Gly
465              470              475              480

Thr Pro Cys Gln Asp Trp Ala Ala Gln Glu Pro His Arg His Ser Ile
                485              490              495

Phe Thr Pro Glu Thr Asn Pro Arg Ala Gly Leu Glu Lys Asn Tyr Cys
            500              505              510

Arg Asn Pro Asp Gly Asp Val Gly Gly Pro Trp Cys Tyr Thr Thr Asn
            515              520              525

Pro Arg Lys Leu Tyr Asp Tyr Cys Asp Val Pro Gln Cys Ala Ala Pro
            530              535              540

Ser Phe Asp Cys Gly Lys Pro Gln Val Glu Pro Lys Lys Cys Pro Gly
545              550              555              560

Arg Val Val Gly Gly Cys Val Ala His Pro His Ser Trp Pro Trp Gln
                565              570              575

Val Ser Leu Arg Thr Arg Phe Gly Met His Phe Cys Gly Gly Thr Leu
            580              585              590

Ile Ser Pro Glu Trp Val Leu Thr Ala Ala His Cys Leu Glu Lys Ser
            595              600              605

Pro Arg Pro Ser Ser Tyr Lys Val Ile Leu Gly Ala His Gln Glu Val
            610              615              620

Asn Leu Glu Pro His Val Gln Glu Ile Glu Val Ser Arg Leu Phe Leu
625              630              635              640

Glu Pro Thr Arg Lys Asp Ile Ala Leu Leu Lys Leu Ser Ser Pro Ala
            645              650              655

Val Ile Thr Asp Lys Val Ile Pro Ala Cys Leu Pro Ser Pro Asn Tyr
            660              665              670

Val Val Ala Asp Arg Thr Glu Cys Phe Ile Thr Gly Trp Gly Glu Thr
            675              680              685

Gln Gly Thr Phe Gly Ala Gly Leu Leu Lys Glu Ala Gln Leu Pro Val
            690              695              700

Ile Glu Asn Lys Val Cys Asn Arg Tyr Glu Phe Leu Asn Gly Arg Val
705              710              715              720

Gln Ser Thr Glu Leu Cys Ala Gly His Leu Ala Gly Gly Thr Asp Ser
                725              730              735

Cys Gln Gly Asp Ser Gly Gly Pro Leu Val Cys Phe Glu Lys Asp Lys
            740              745              750

Tyr Ile Leu Gln Gly Val Thr Ser Trp Gly Leu Gly Cys Ala Arg Pro
            755              760              765

Asn Lys Pro Gly Val Tyr Val Arg Val Ser Arg Phe Val Thr Trp Ile
            770              775              780

Glu Gly Val Met Arg Asn Asn
785              790
```

<210> SEQ ID NO 34
<211> LENGTH: 250
<212> TYPE: PRT
<213> ORGANISM: Homo sapiens -continued

```
<400> SEQUENCE: 34

Ala Ala Pro Ser Phe Asp Cys Gly Lys Pro Gln Val Glu Pro Lys Lys
1               5                   10                  15

Cys Pro Gly Arg Val Val Gly Gly Cys Val Ala His Pro His Ser Trp
            20                  25                  30

Pro Trp Gln Val Ser Leu Arg Thr Arg Phe Gly Met His Phe Cys Gly
        35                  40                  45

Gly Thr Leu Ile Ser Pro Glu Trp Val Leu Thr Ala Ala His Cys Leu
    50                  55                  60

Glu Lys Ser Pro Arg Pro Ser Ser Tyr Lys Val Ile Leu Gly Ala His
65                  70                  75                  80

Gln Glu Val Asn Leu Glu Pro His Val Gln Glu Ile Glu Val Ser Arg
                85                  90                  95

Leu Phe Leu Glu Pro Thr Arg Lys Asp Ile Ala Leu Leu Lys Leu Ser
            100                 105                 110

Ser Pro Ala Val Ile Thr Asp Lys Val Ile Pro Ala Cys Leu Pro Ser
        115                 120                 125

Pro Asn Tyr Val Val Ala Asp Arg Thr Glu Cys Phe Ile Thr Gly Trp
    130                 135                 140

Gly Glu Thr Gln Gly Thr Phe Gly Ala Gly Leu Leu Lys Glu Ala Gln
145                 150                 155                 160

Leu Pro Val Ile Glu Asn Lys Val Cys Asn Arg Tyr Glu Phe Leu Asn
            165                 170                 175

Gly Arg Val Gln Ser Thr Glu Leu Cys Ala Gly His Leu Ala Gly Gly
            180                 185                 190

Thr Asp Ser Cys Gln Gly Asp Ser Gly Gly Pro Leu Val Cys Phe Glu
            195                 200                 205

Lys Asp Lys Tyr Ile Leu Gln Gly Val Thr Ser Trp Gly Leu Gly Cys
    210                 215                 220

Ala Arg Pro Asn Lys Pro Gly Val Tyr Val Arg Val Ser Arg Phe Val
225                 230                 235                 240

Thr Trp Ile Glu Gly Val Met Arg Asn Asn
            245                 250
```